(12) United States Patent
Klemm et al.

(10) Patent No.: US 9,365,343 B2
(45) Date of Patent: Jun. 14, 2016

(54) DISPENSER WITH MOTOR, GEAR PLATE, AND SNAP FIT CAP

(75) Inventors: Robert Klemm, Colgate, WI (US); Wai Kei Leung, Yuen Long (HK)

(73) Assignee: S. C. Johnson & Sons, Inc., Racine, WI (US)

( * ) Notice: Subject to any disclaimer, the term of this patent is extended or adjusted under 35 U.S.C. 154(b) by 858 days.

(21) Appl. No.: 13/409,759

(22) Filed: Mar. 1, 2012

(65) Prior Publication Data

US 2012/0223625 A1 Sep. 6, 2012

Related U.S. Application Data

(60) Provisional application No. 61/448,108, filed on Mar. 1, 2011.

(51) Int. Cl.

| | |
|---|---|
| *H02K 7/10* | (2006.01) |
| *B65D 83/26* | (2006.01) |
| *H02K 11/00* | (2016.01) |
| *H02K 7/116* | (2006.01) |
| *A47K 5/12* | (2006.01) |
| *A61L 9/14* | (2006.01) |
| *B05B 9/08* | (2006.01) |
| *A61L 2/22* | (2006.01) |

(52) U.S. Cl.
CPC ............. *B65D 83/262* (2013.01); *H02K 7/116* (2013.01); *H02K 11/0068* (2013.01); *H02K 11/30* (2016.01); *A47K 5/1217* (2013.01); *A61L 2/22* (2013.01); *A61L 9/14* (2013.01); *A61L 2202/25* (2013.01); *A61L 2202/26* (2013.01); *B05B 9/0805* (2013.01)

(58) Field of Classification Search
CPC ........... H02K 7/116; H02K 7/10; H02K 5/04; H02K 5/00; H02K 2205/00; H02K 2207/00; H02K 1/18; H02K 11/0068; H02K 7/1163; H02K 7/1166; F16F 2226/044; B65D 83/262; A47K 5/1217; B05B 12/122
USPC .............................. 310/68 R, 83, 75 R, 96, 99
See application file for complete search history.

(56) References Cited

U.S. PATENT DOCUMENTS

| | | |
|---|---|---|
| 3,139,218 A | 6/1964 | Cairelli |
| 3,150,800 A | 9/1964 | Weber, III |
| 3,165,238 A | 1/1965 | Wiley |
| 3,179,296 A | 4/1965 | Cairelli |
| 3,329,314 A | 7/1967 | Kolodziej |
| 3,376,758 A * | 4/1968 | Mackay ...................... 74/421 R |

(Continued)

FOREIGN PATENT DOCUMENTS

| | | |
|---|---|---|
| CN | 2276836 Y | 3/1998 |
| CN | 2374277 Y | 4/2000 |

(Continued)

OTHER PUBLICATIONS

Machine Translation of FR 2505572.*

(Continued)

*Primary Examiner* — Michael Andrews

(57) ABSTRACT

An assembly including a drive motor and a gear plate. The gear plate includes a seat for retaining the drive motor. The assembly also includes a motor cap having at least one pawl for snap-fitting into the seat. The assembly further includes at least one post, which is adapted to receive a gear.

20 Claims, 20 Drawing Sheets

(56) References Cited

U.S. PATENT DOCUMENTS

| | | | |
|---|---|---|---|
| 3,676,725 A * | 7/1972 | Wiser et al. | 310/83 |
| 4,625,134 A * | 11/1986 | Weaver | H02K 7/116 310/83 |
| 5,038,972 A | 8/1991 | Muderlak et al. | |
| 5,357,818 A | 10/1994 | Hill | |
| 5,676,283 A * | 10/1997 | Wang | G04C 23/42 222/648 |
| 7,011,795 B2 | 3/2006 | Thompson et al. | |
| 7,573,167 B2 | 8/2009 | Miyamoto et al. | |
| 7,691,336 B2 | 4/2010 | Westring | |
| 8,261,950 B2 | 9/2012 | Cittadino et al. | |
| 2003/0156366 A1* | 8/2003 | Horng | H02K 5/1675 361/23 |
| 2006/0017454 A1* | 1/2006 | Bhatti | 324/765 |
| 2006/0082246 A1* | 4/2006 | Robin et al. | 310/239 |
| 2008/0036316 A1* | 2/2008 | Miyamoto | H02K 7/116 310/71 |
| 2008/0150401 A1* | 6/2008 | Lin et al. | 310/67 R |
| 2010/0226836 A1 | 9/2010 | Thur et al. | |

FOREIGN PATENT DOCUMENTS

| | | | |
|---|---|---|---|
| DE | 2326293 A1 | 12/1973 | |
| EP | 0089214 A1 | 9/1983 | |
| EP | 0719234 B1 | 7/1996 | |
| EP | 1352562 B1 | 10/2003 | |
| EP | 1370304 B1 | 12/2003 | |
| EP | 1407790 A1 | 4/2004 | |
| EP | 1547505 B1 | 6/2005 | |
| EP | 1586335 B1 | 10/2005 | |
| EP | 1695720 B1 | 8/2006 | |
| EP | 1997519 A1 | 12/2008 | |
| FR | 2036157 | 12/1970 | |
| FR | 2505572 A1 * | 11/1982 | H02K 7/116 |
| GB | 1160537 | 8/1969 | |
| GB | 2094407 A | 9/1982 | |
| GB | 2287725 A | 9/1995 | |
| GB | 2314890 A | 1/1998 | |
| GB | 2436918 A | 10/2007 | |
| JP | 3033850 A | 2/1991 | |
| KR | 10-0156752 | 12/1998 | |
| KR | 10-0676413 | 2/2007 | |
| KR | 10-2007-0083060 | 8/2007 | |
| WO | WO01/25730 A1 | 4/2001 | |
| WO | WO2006/074454 A3 | 7/2006 | |
| WO | WO2006/114532 A1 | 11/2006 | |
| WO | WO2007/132140 A1 | 11/2007 | |
| WO | WO2008/037103 A1 | 4/2008 | |
| WO | WO2008/149064 A1 | 12/2008 | |
| WO | WO2008/149065 A1 | 12/2008 | |
| WO | WO2008/149066 A1 | 12/2008 | |
| WO | WO20091062553 A1 | 5/2009 | |
| WO | WO2009/130927 A1 | 10/2009 | |
| WO | WO2010/101455 A2 | 9/2010 | |

OTHER PUBLICATIONS

Machine translation of FR2505572A1 (Nov. 1982).*
International Preliminary Report on Patentability dated Sep. 3, 2013, International App. No. PCT/US2012/027210, 5 pages.
PCT/US2012/027210 International Search Report dated May 30, 2012.
International Search Report mailed May 30, 2012 for PCT/US2012/027210, 4 pages.

* cited by examiner

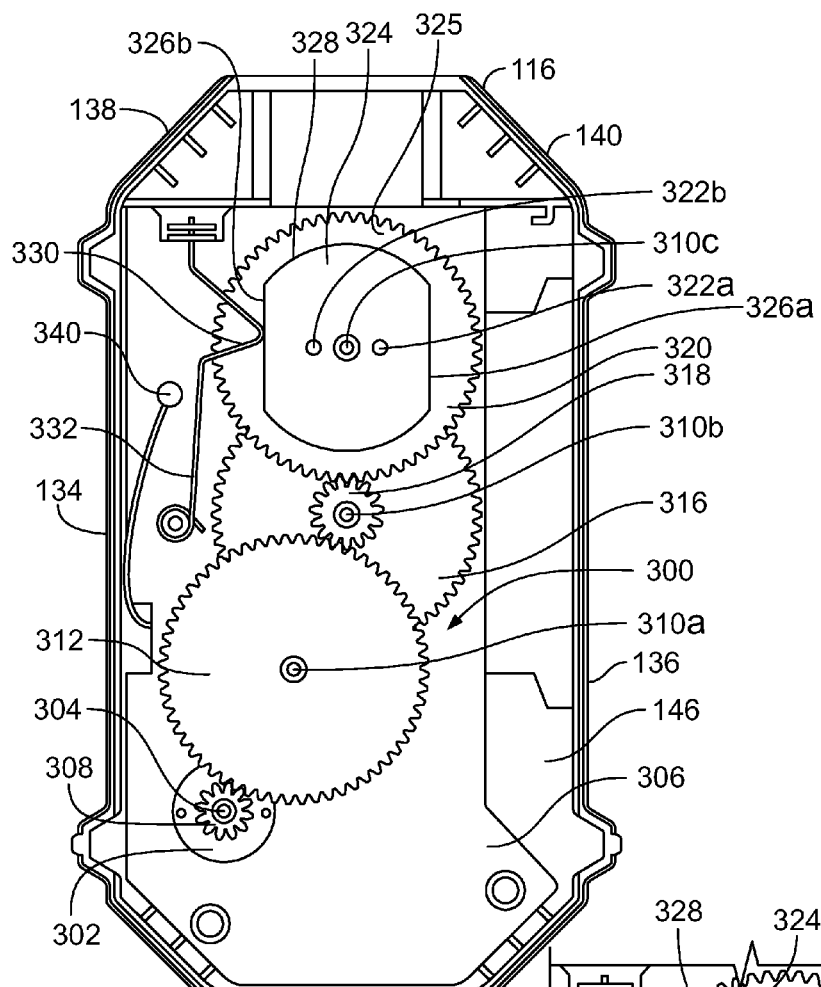
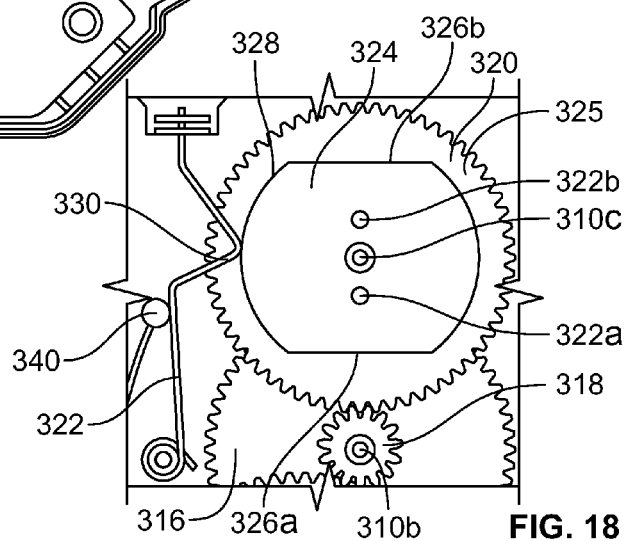
FIG. 17
FIG. 18

DISPENSER WITH MOTOR, GEAR PLATE, AND SNAP FIT CAP

CROSS REFERENCE TO RELATED APPLICATIONS

This application claims the benefit of U.S. Provisional Application No. 61/448,108 filed on Mar. 1, 2011.

REFERENCE REGARDING FEDERALLY SPONSORED RESEARCH OR DEVELOPMENT

Not applicable

SEQUENTIAL LISTING

Not applicable

BACKGROUND OF THE INVENTION

1. Field of the Background

The present disclosure relates to drive module assemblies for use in dispensers that discharge volatile materials from an aerosol container and method of making same.

2. Description of the Background

A drive module assembly for discharging a fluid from an aerosol container within a dispenser is typically assembled piece-by-piece directly into the housing of the dispenser. The drive module assemblies are not inserted into the dispenser as a whole assembled unit and cannot be removed as a single unit. Additionally, components of the drive module assemblies are traditionally attached together by way of screws, bolts, or other similar fasteners.

Thompson et al. U.S. Pat. No. 7,011,795 discloses a device for dispersing scented materials into an environment. The device includes a drive assembly mounted within a bottom housing of the device and includes a motor and gear train. The pieces of the drive assembly, i.e. the motor and the gears are separately inserted into the housing of the device. Additionally, the motor is mounted directly to the housing by a motor retainer, which appears to include a hole for a fastener such as a screw to secure the motor in the housing.

These prior devices fail to provide drive assemblies that are easy and labor efficient to manufacture and assemble. Additionally, the prior art devices fail to provide drive module assemblies that are assembled as a whole before being singularly inserted into a dispenser, providing manufacturers with less ability to change the design of the dispensers without having to redesign the drive assembly.

SUMMARY OF THE INVENTION

According to one embodiment, a drive module assembly includes a drive motor and a gear plate with a seat for retaining the motor. The assembly also includes a motor cap having at least one pawl for snap-fitting into the seat. The assembly further includes at least one axle, which is adapted to receive a gear.

According to another embodiment, a method for assembling a drive module includes the step of providing a gear plate with a seat for a motor and at least one axle. Further, the method includes the steps of retaining the motor within the seat, providing a motor cap with at least one pawl, wherein the at least one pawl snaps into the seat, and disposing a gear train on the at least one axle.

According to a different embodiment, a dispensing system includes a housing, a container having a product therein, and a drive module assembly adapted to release product from the dispensing system. The drive module assembly includes a drive motor and a gear plate with a seat for retaining the motor. The drive module assembly also includes a motor cap having two pawls disposed on a bottom side for snap-fitting into the seat, and two pawls extending from an upper surface thereof. The drive module assembly further includes at least one axle adapted to receive a gear.

Other aspects and advantages will become apparent upon consideration of the following detailed description and the attached drawings, in which like elements are assigned like reference numerals.

BRIEF DESCRIPTION OF THE DRAWINGS

FIG. 17 is a rear elevational view of a fourth embodiment of a drive module assembly disposed in a dispenser;

FIG. 18 is a partial rear elevational view of the drive module assembly of FIG. 17, with a switch in a closed position;

DETAILED DESCRIPTION OF THE DRAWINGS

Figure 1:
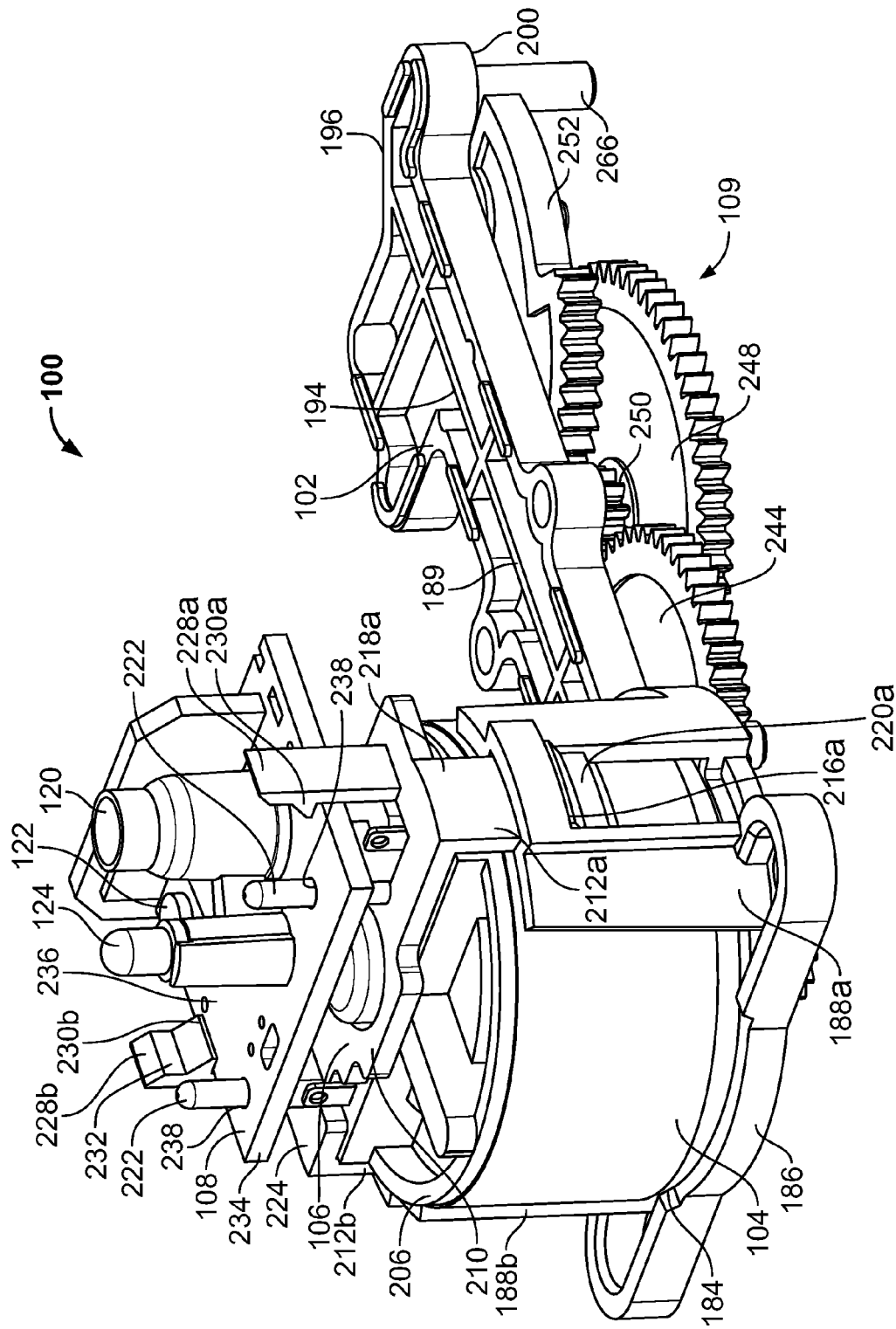
FIG. 1 is an isometric view of a first embodiment of a drive module assembly including a gear plate, a motor, a motor cap, a printed circuit board assembly, and a gear train.

FIGS. 1-4 depict a first embodiment of a drive module assembly 100. The drive module assembly 100 generally includes an integral gear plate 102, a snap-in motor 104, a motor cap 106, a printed circuit board assembly ("PCBA") 108, and a gear train 109. The drive module assembly 100 is designed to be utilized in a dispenser 110 (shown in FIGS. 5-13) for dispensing the contents of a container 112. The container 112 may be an aerosol container or a pump-type sprayer of any size and volume known to those skilled in the art. However, the container 112 is preferably an aerosol container having a valve assembly (not shown), which includes a valve stem 114. The dispenser 110 may be one of the devices described in Carpenter et al. U.S. patent application Ser. No. 11/725,402, which is incorporated herein by reference in its entirety.

Still referring to FIGS. 5-13, the dispenser 110 generally includes a housing 116 that is adapted to receive the drive module assembly 100, the aerosol container 112, and batteries 118. In addition, the dispenser 110 includes a sensor 120, one or more input devices 122 (shown in FIG. 1) such as switches, dials, keypads, pushbuttons, etc., a light source 124, e.g., a light emitting diode ("LED"), an actuator arm 126, and a housing cover 128. The sensor 120 in the present embodiment is a photocell light sensor, which may be used to detect motion. However, any other type of motion detector may be utilized, e.g., a passive infrared or pyroelectric motion sensor, an infrared reflective motion sensor, an ultrasonic motion sensor, or a radio or microwave radio motion sensor. Further, the sensor 120 can be replaced or used in combination with any other type of sensor known to those skilled in the art, e.g., a heat sensor or an odor sensor.

Figure 6:
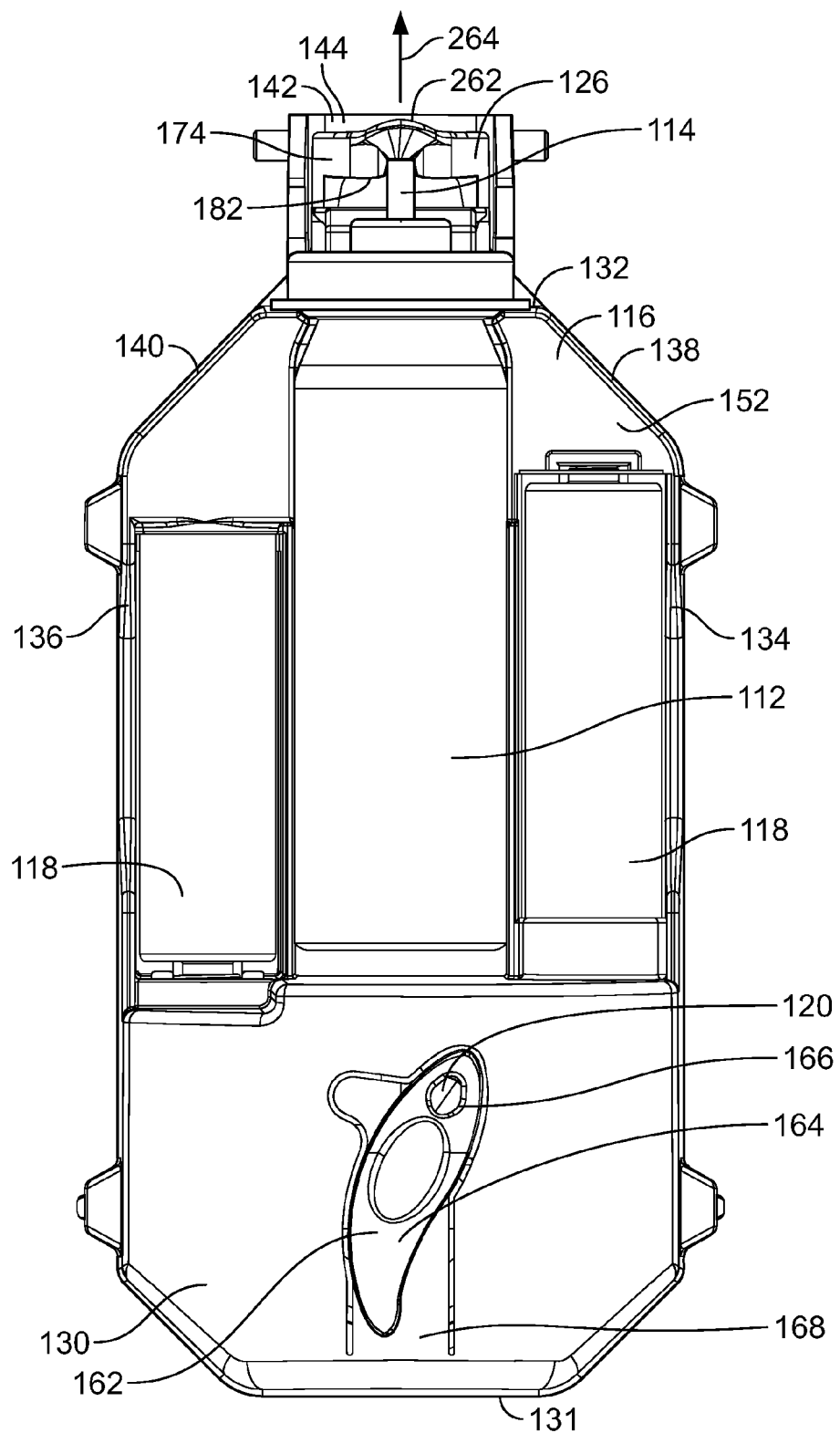
FIG. 6 is a front elevational view of the dispenser of FIG. 5 wherein a cover has been omitted for clarity.

Turning to FIG. 6, the housing 116 of the dispenser 110 comprises a base portion 130 and a top portion 132. First and second sidewalls 134, 136, respectively, extend between the base portion 130 and the top portion 132. Further, the top portion 132 includes first and second shoulders 138, 140, respectively, wherein the first shoulder 138 extends inwardly from the first sidewall 134 and the second shoulder 140 extends inwardly from the second sidewall 136. The present embodiment also includes an actuator arm cover 142 that extends upwardly from the top portion 132 to cover the actuator arm 126, however, the actuator arm cover 142 could be omitted. In a preferred embodiment, the actuator arm cover 142 is contoured to have a shape similar to that of the actuator arm 126. The top portion 132 also includes a channel 144, wherein the channel 144 is disposed between an inner rear panel 146 (see FIG. 10) and an outer rear panel 148 of the housing 116 (see FIG. 12).

Figure 5:
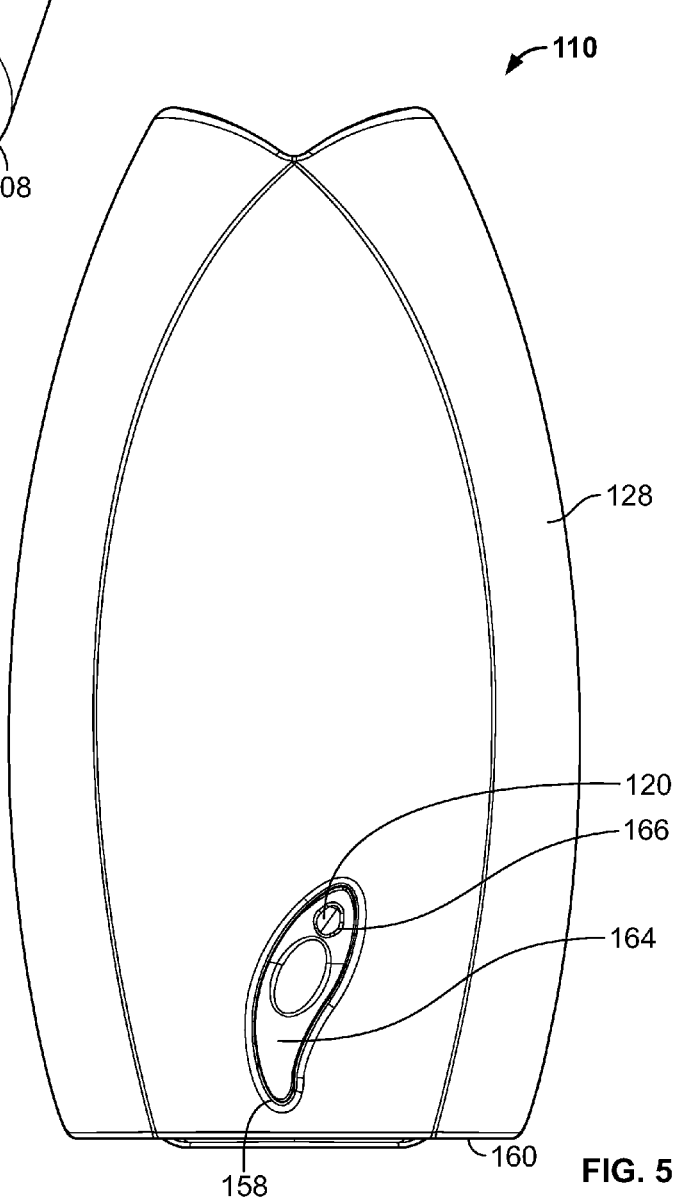
FIG. 5 is a front elevational view of a dispenser, which uses the drive module assembly of FIG. 1.
Figure 7:
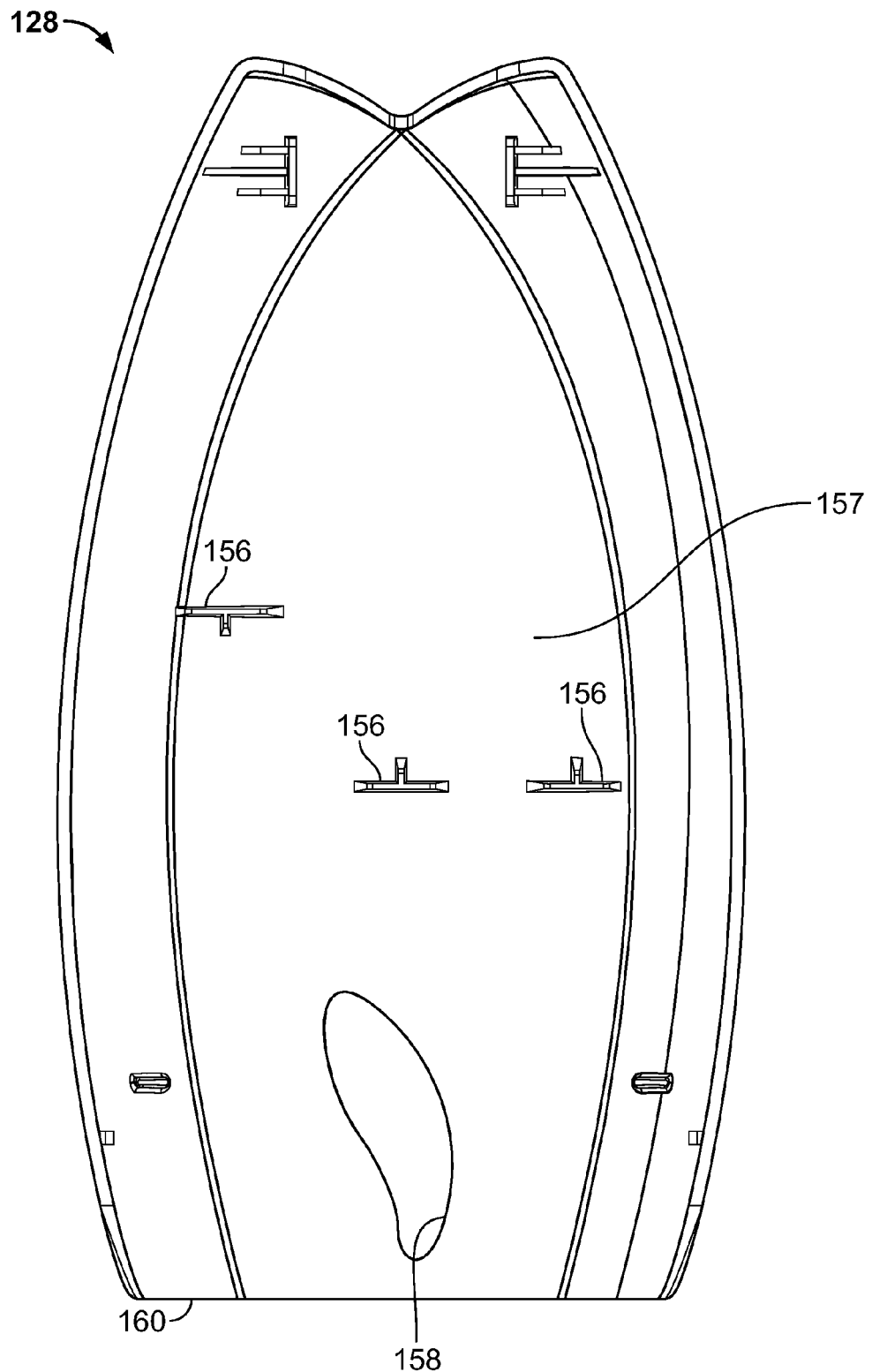
FIG. 7 is a rear elevational view of the cover.
Figure 8:
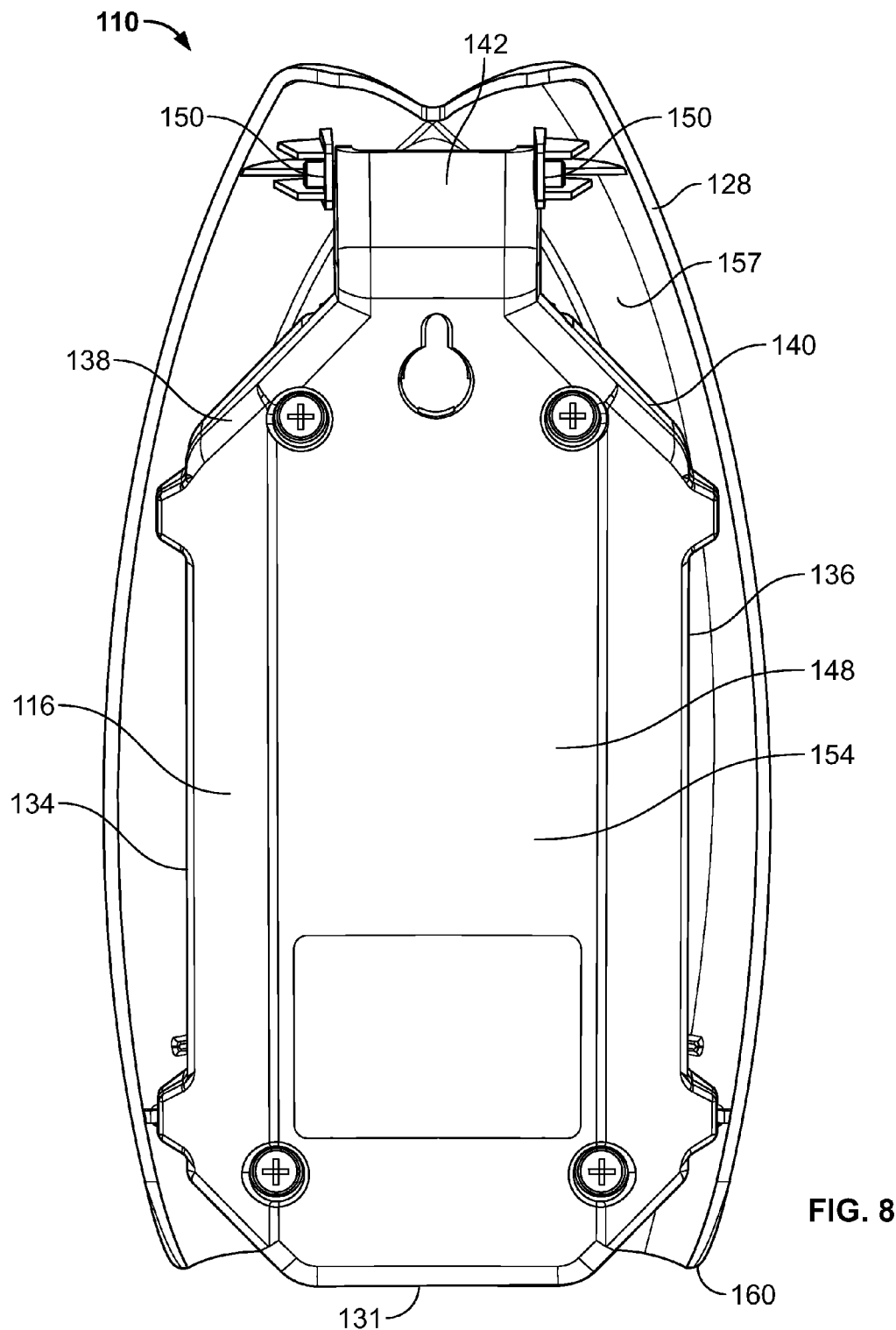
FIG. 8 is a rear elevational view of the dispenser of FIG. 5.

Referring now to FIGS. 5, 7, and 8, the housing cover 128 is pivotally attached to the housing 116 by a hinge 150. The cover 128 wraps around the side walls 134, 136, the top portion 132, the actuator arm 126, and a front side 152 of the housing 116 in a closed condition, thereby leaving a bottom end 131 of the base portion 130 and the rear side 154 of the housing 116 exposed. The cover 128 is moved to an open position by rotating same about the hinge 150. The cover 128 may include a plurality of posts 156 extending from an inner surface 157 thereof, for retaining the batteries 118 and/or the container 112 when the cover 128 is closed. The cover 128 also includes a generally teardrop shaped orifice 158 provided in a lower end 160 thereof. A similarly shaped button 162 extends through the orifice 158 and projects outwardly from the cover 128. The button 162 includes a top surface 164 for engagement by a user's thumb or finger. A curved orifice 166 is disposed within the top surface 164 of the button 162. The orifice 166 is aligned with the sensor 120 disposed within the base portion 130 of the housing 116. The button 162 is provided for activating the dispenser 110 to emit fluid upon the depression of same. The button 162 is attached to the front side 152 of the housing 116 by way of a living hinge 168 (see FIG. 6), wherein the depression and/or rotation of the button 162 about the living hinge 168 causes a switch 122 (shown in FIG. 1) to generate a signal and the dispenser 110 to discharge fluid during manual activation. The button 162 is made of a material, which allows the LED 124 to be viewable through the button 162. In other embodiments it is contemplated that the cover 128 may be adapted to include an LED port through which to view the LED 124.

Figure 9:
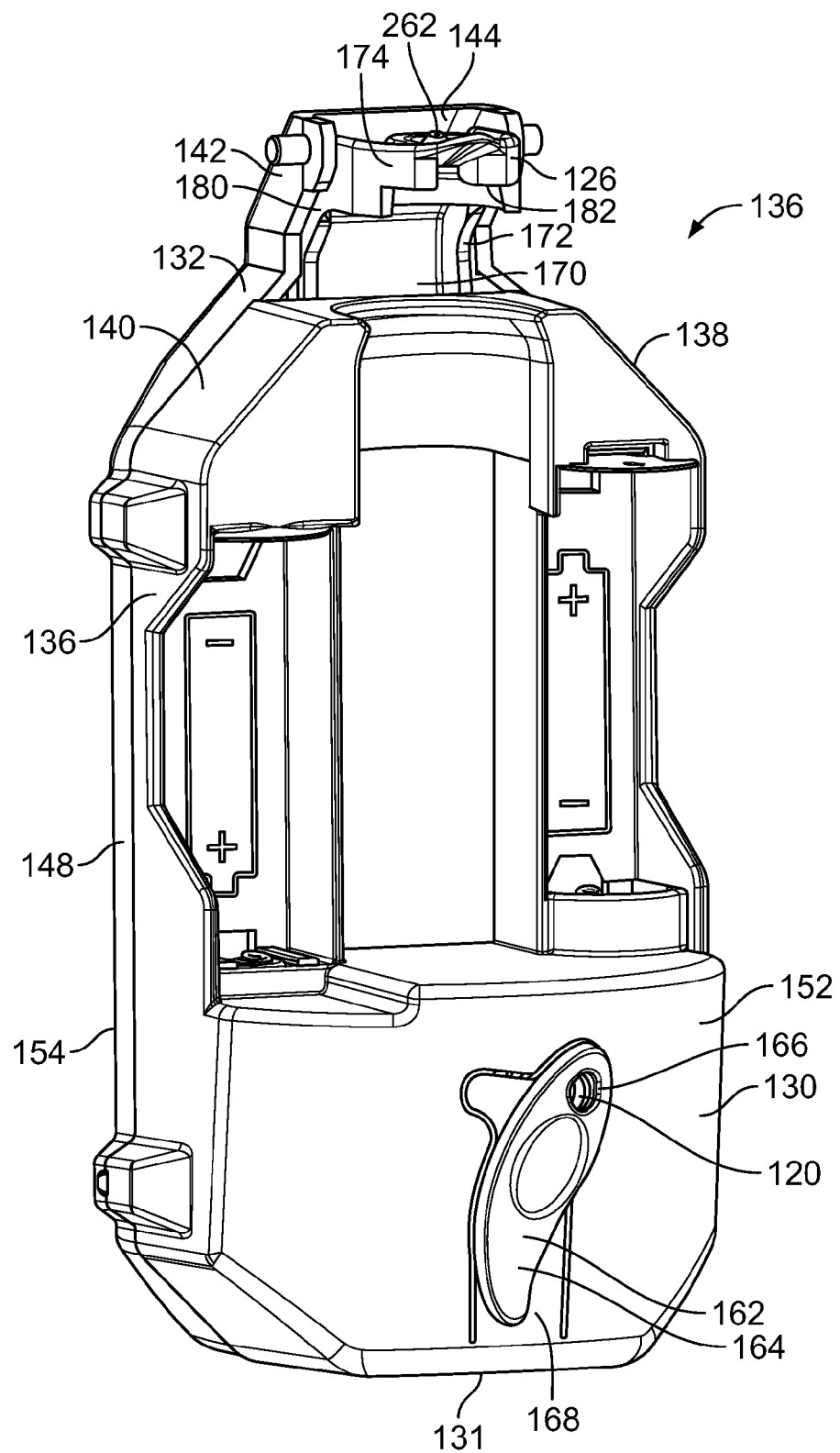
FIG. 9 is an isometric view of the front, top, and left side of the dispenser of FIG. 5 wherein a cover, batteries, and container have been removed for clarity.
Figure 10:
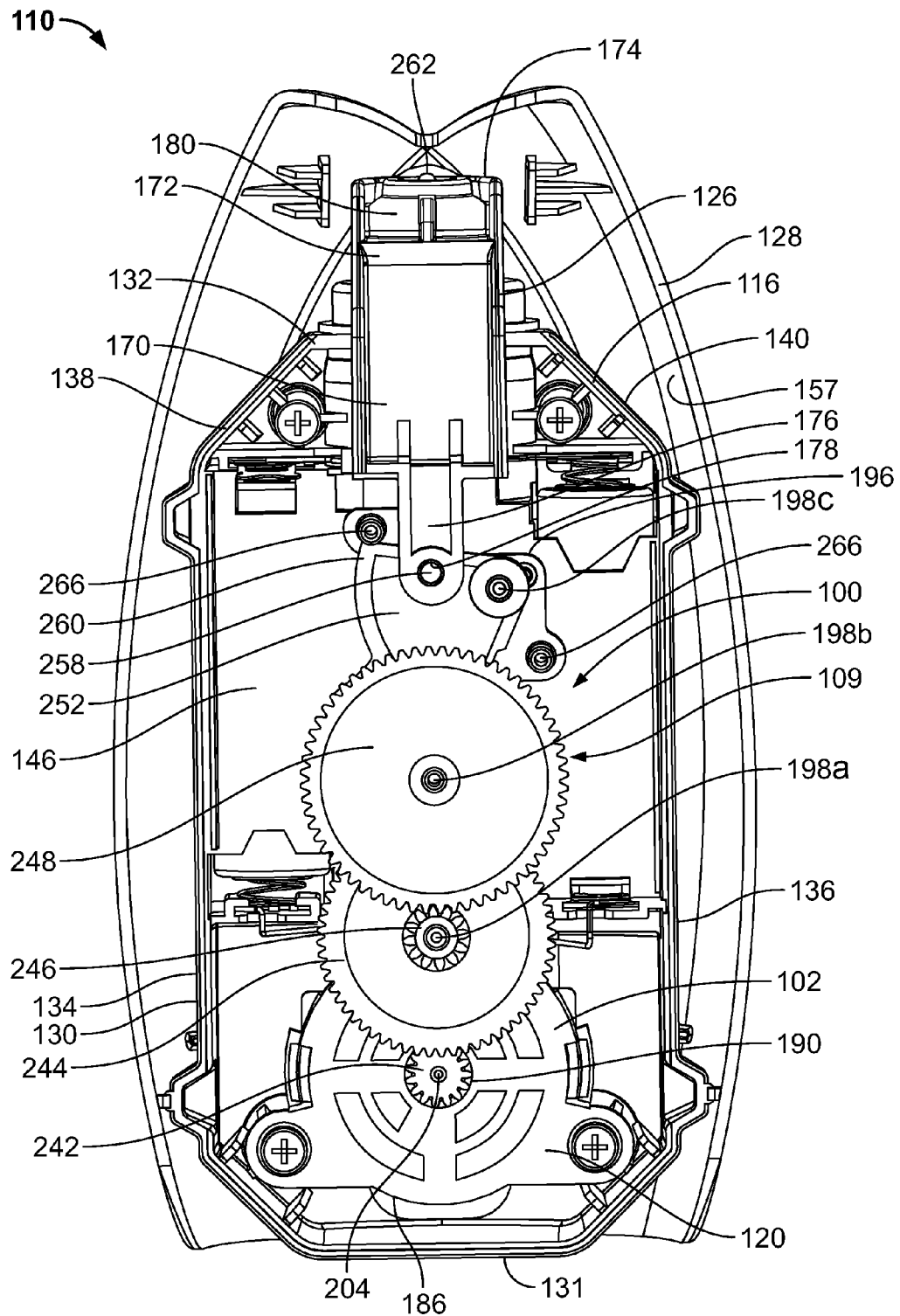
FIG. 10 is a rear elevational view of the dispenser of FIG. 5 wherein a rear panel has been removed.
Figure 11:
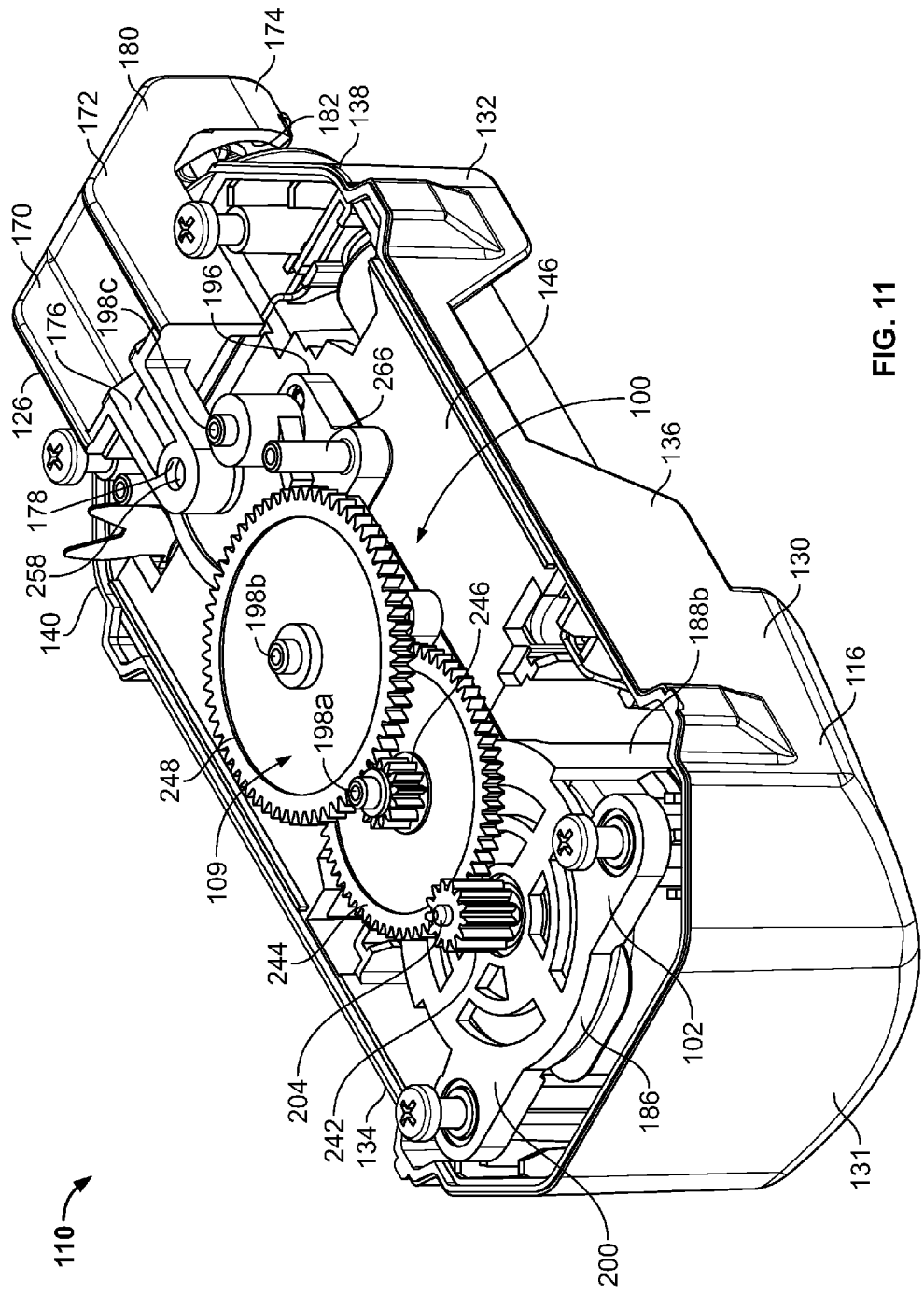
FIG. 11 is an isometric view of the dispenser of FIG. 10 wherein the rear panel has been removed for clarity.
Figure 12:
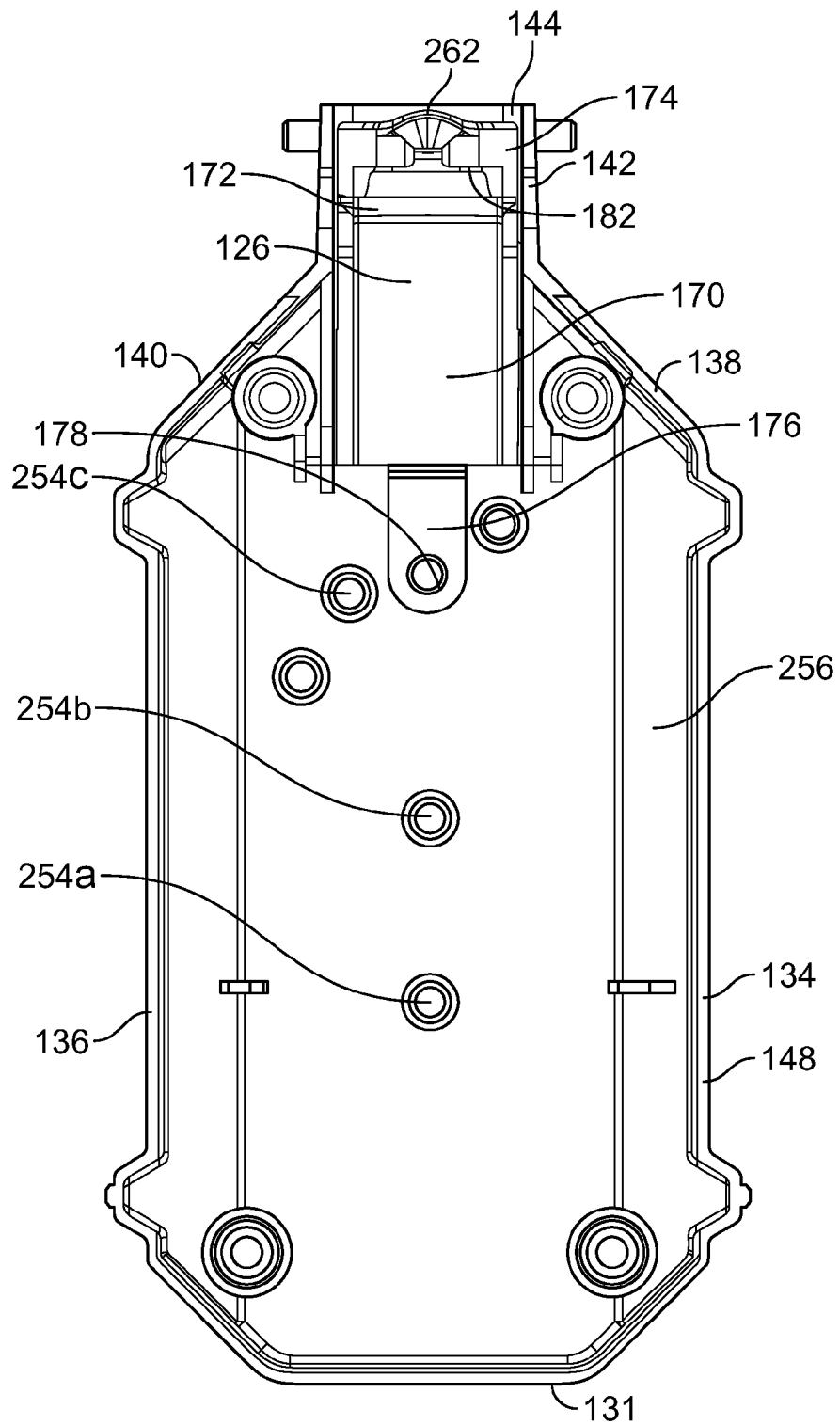
FIG. 12 is a front elevational view of the rear panel and actuator arm of the dispenser of FIG. 5.
Figure 13:
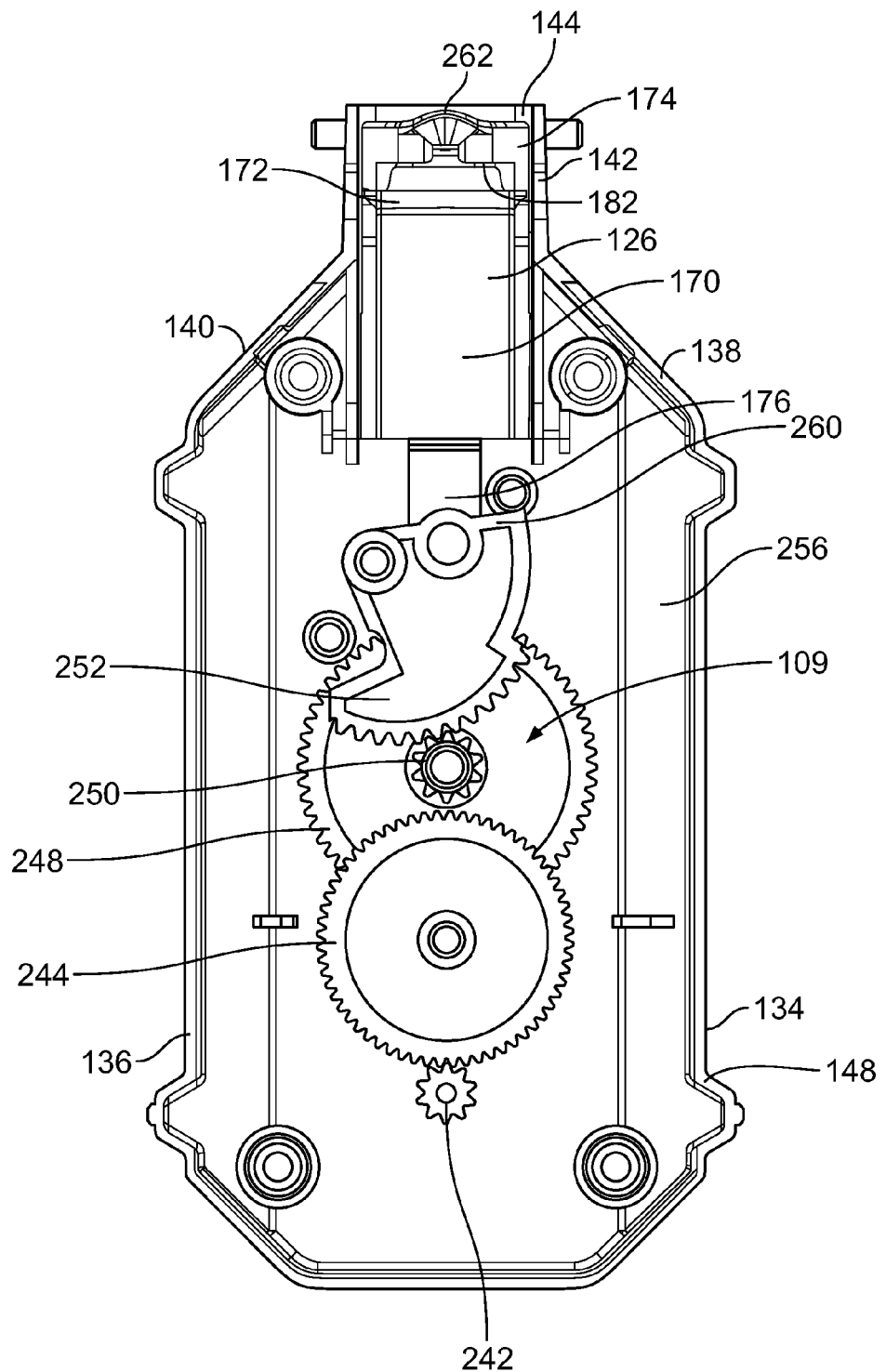
FIG. 13 is a front elevational view of the rear panel of the dispenser of FIG. 5 including the actuator arm and gear train.

With regards to FIGS. 9-11, the actuator arm 126 includes a main portion 170, an intermediate portion 172, and an overhang portion 174. A depending attachment portion 176 that includes a circular aperture 178 extends downwardly from the main portion 170. The attachment portion 176 is coupled to a section of the drive module assembly 100, as noted in greater detail hereinafter. The main portion 170 is disposed within the channel 144 and is substantially parallel with the outer rear panel 148 of the housing 116. The intermediate portion 172 of the actuator arm 126 extends laterally and upwardly from the main portion 170. An upper end 180 of the intermediate portion 172 is therefore farther from the outer rear panel 148 and the top portion 132 of the housing 116 than the main portion 170. The overhang portion 174 of the actuator arm 126 extends from the upper end 180 of the intermediate portion 172 toward the front side 152 of the housing 116. The overhang portion 174 is substantially transverse to the main portion 170.

Prior to opening the valve assembly and releasing the contents of the container 112, the overhang portion 174 of the actuator arm 126 is positioned in a pre-actuation position (see FIG. 6). Preferably, when the actuator arm 126 and the overhang portion 174 are positioned in a pre-actuation position, a distal end of the valve stem 114 is spaced slightly from or just in contact with a lower side 182 of the overhang portion 174. Alternatively, at this point, the overhang portion 174 may partially depress the valve stem 114 a distance insufficient to open the valve stem 114. The actuator arm 126 depresses the valve stem 114 through motion imparted thereto by the module drive assembly 100 as described below.

The dispenser 110 discharges fluid from the container 112 upon occurrence of a particular condition. The condition could be the manual activation of the dispenser 110 or the automatic activation of the dispenser 110 in response to an elapsed time interval or signal from the sensor 120. The fluid may be a fragrance or insecticide disposed within a carrier liquid, a deodorizing liquid, or the like. For example, the fluid may comprise OUST®, an air and carpet sanitizer for household, commercial, and institutional use, or GLADE®, a household deodorant, both sold by S. C. Johnson and Son, Inc., of Racine, Wis. The fluid may also comprise other actives, such as sanitizers, air fresheners, odor eliminators, mold or mildew inhibitors, insect repellents, and the like, or that have aromatherapeutic properties. The fluid alternatively comprises any fluid known to those skilled in the art that can be dispensed from a container. The dispenser 110 is therefore adapted to dispense any number of different fluid formulations.

Referring again to FIGS. 1-4, the various components of the drive module assembly 100 will be described. The gear plate 102 includes a seat 184 located at a first end 186 thereof. The seat 184 includes two opposing curved support members 188a, 188b extending upwardly from an upper surface 189 of the gear plate 102. A circular aperture 190 is disposed in the gear plate 102 between the curved support walls 188a, 188b. Additionally, two pins 192 (only one pin is shown) extend upwardly from the seat 184 of the integral gear plate 102. An elongate section 194 of the gear plate 102 extends from the seat 184 to a second end 196 of the integral gear plate 102. A plurality of axles 198a, 198b, 198c extend from an underside 200 of the gear plate 102. The axles 198a-c are designed to receive a plurality of gears of the gear train 109 for driving the dispenser 110. In this embodiment, there are three axles, but any number of axles may be used in conjunction with any gear train capable of driving the dispenser 110.

Figure 3:
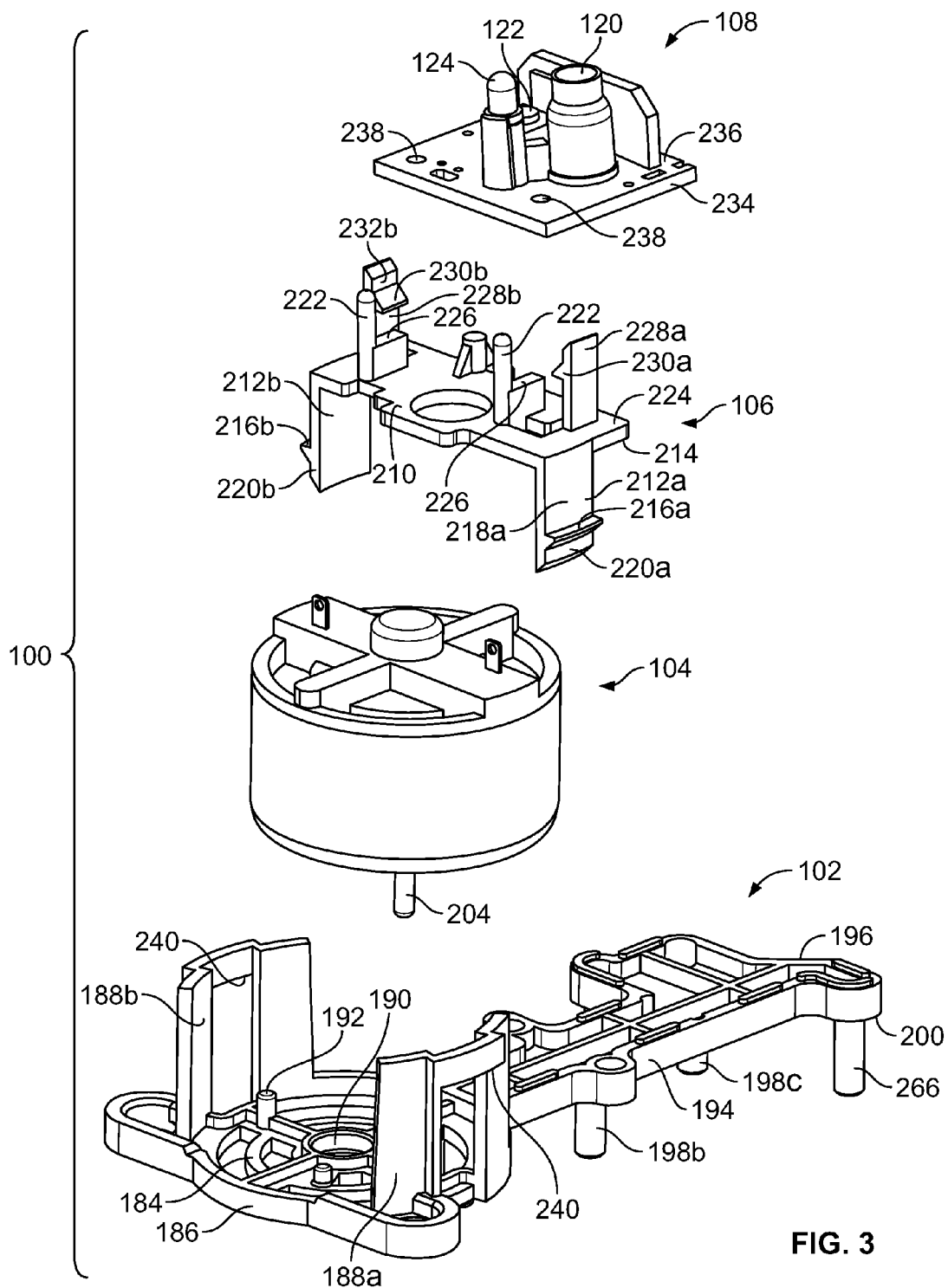
FIG. 3 is an exploded isometric view of the drive module assembly of FIG. 1 wherein the gear train is omitted.
Figure 4:
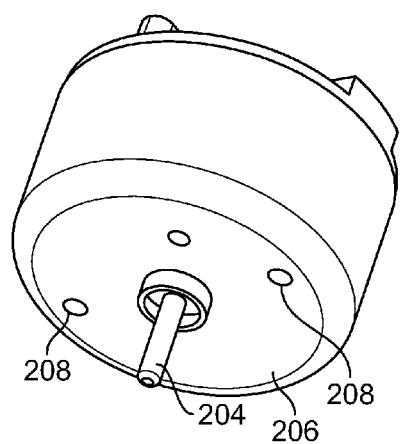
FIG. 4 is an isometric view of the front, bottom, and left side of the motor of FIG. 1.

As shown in FIGS. 3 and 4, the motor 104 includes a drive shaft 204 extending from a front side 206, thereof. The motor 104 also includes two holes 208 disposed in the front side 206 of the motor 104. The holes 208 are designed to receive the pins 192 located on the gear plate 102.

Still referring to FIG. 3, the motor cap 106 includes a horizontal platform 210 with two opposing arms 212a, 212b depending from a bottom 214 of the platform 210. The depending arms 212a, 212b include snap-in pawls 216a, 216b disposed on outer surfaces 218a, 218b of the arms 212a, 212b, respectively. Leader guide surfaces 220a, 220b are disposed on distal ends of the depending arms 212a, 212b, respectively. The motor cap 106 also includes two guide posts 222 extending upwardly from an upper surface 224 of the horizontal platform 210. Two axial restraining surfaces 226 are disposed adjacent the guide posts 222 on the horizontal platform 210. Additionally, two opposing PCBA supports 228a, 228b extend upwardly from the upper surface 224 of the horizontal platform 210. The PCBA supports 228a, 228b include snap-in pawls 230a, 230b disposed on inner surfaces 232a, 232b (only 232b is shown, 232a being a mirror image thereof) of the PCBA supports 228a, 228b, respectively.

Figure 2:
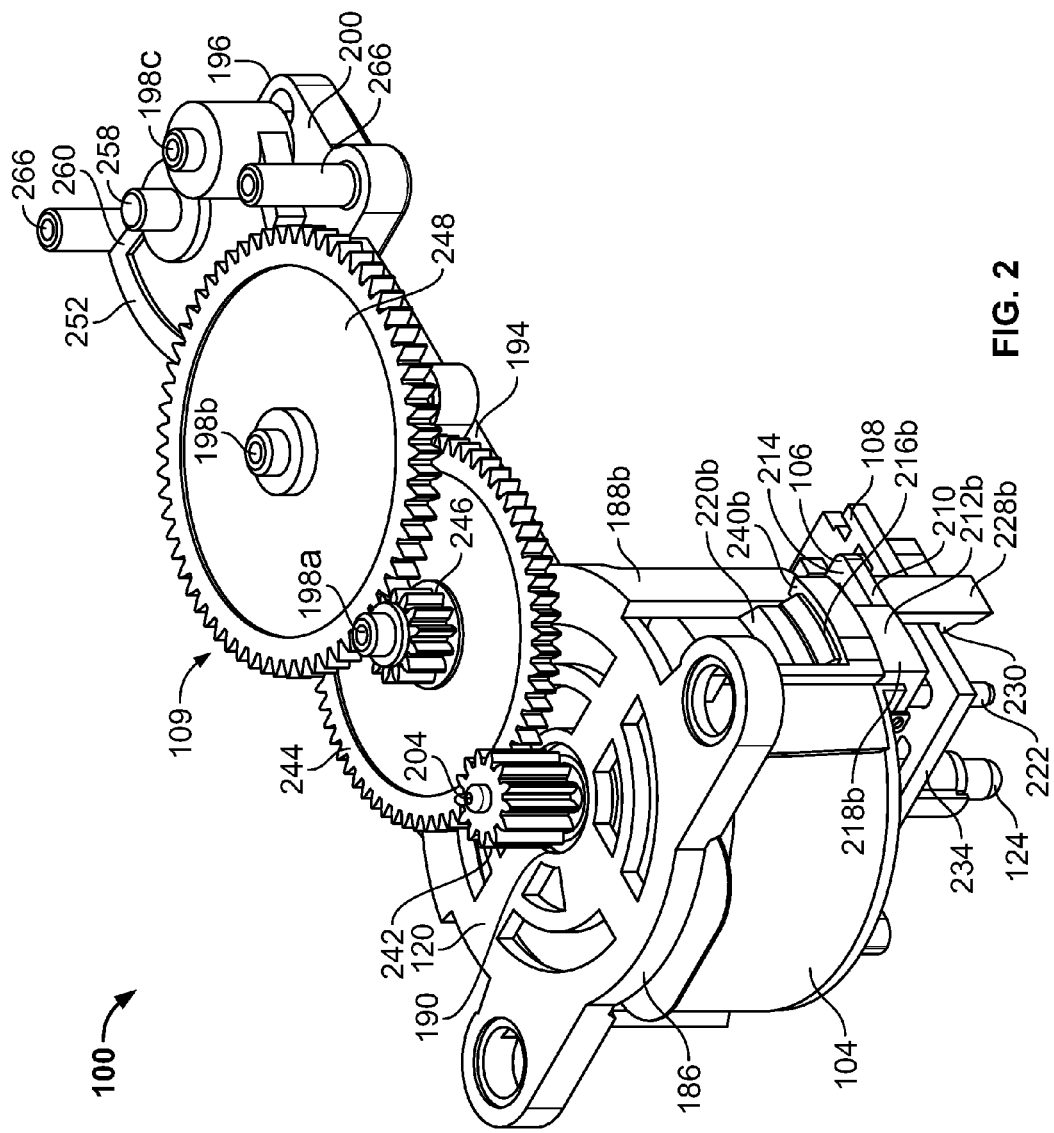
FIG. 2 is an isometric view of the drive module assembly of FIG. 1.

Referring now to FIGS. 1-3, the PCBA 108 includes a board 234 with the actuation switch 122, the LED 124, and the sensor 120 disposed on an upper surface 236 of the board 234. The PCBA 108 further includes two holes 238 provided in the board 234.

In an assembled position, the motor 104 is disposed between the curved support members 188a, 188b on the seat 184 of the integral gear plate 102. The drive shaft 204 of the motor 104 extends through the circular aperture 190 in the seat 184 when the motor 204 is seated on the integral gear plate 102. The holes 208 in the front side 206 of the motor 104 receive the two pins 192 located on the integral gear plate 102. The holes 208 and pins 192 are designed to torsionally restrain the motor 104 within the gear plate 102, to prevent the motor 104 from rotating during operation. After the motor 104 is disposed within the seat 184, the motor cap 106 is inserted over the motor 104, thereby locking the motor 104 in place within the seat 184 of the integral gear plate 102 without the need for screws. The leader guide surfaces 220a, 220b align the depending arms 212a, 212b of the motor cap 106 with the supports 188a, 188b, respectively, on the integral gear plate 102. When the arms 212a, 212b and supports 188a, 188b are properly aligned, the pawls 216a, 216b are able to snap into snap-fit engagement portions 240a, 240b located on the supports 188a, 188b, respectively. The pawls 216a, 216b retain the motor cap 106 over the motor 104, thereby locking the motor 104 in place on the integral gear plate 102. Although this embodiment uses snap in pawls 216a, 216b to attach the motor cap 106 to the integral gear plate 102, it is contemplated that other snapping engagement mechanisms may be used to attach the motor cap 106 to the gear plate 102 to restrain the motor 104 without screws.

When the motor cap 106 is attached to the integral gear plate 102 the PCBA 108 is aligned and attached to the upper surface 224 of the motor cap 106. The holes 238 in the board 234 align and receive the guide posts 222 of the motor cap 106. The guide posts 222 ensure that the LED 124, the sensor 120, and the switch 122 located on the board 234 properly align with the housing 116 of the dispenser 110, when the drive module assembly 100 is inserted into the dispenser 110. As the PCBA 108 is inserted onto the motor cap 106, the PCBA supports 228a, 228b deflect outwardly to allow the PCBA 108 to pass by the pawls 230a, 230b and sit on the axial retaining surfaces 226 of the motor cap 106. After the PCBA 108 passes the pawls 230a, 230b, the supports 228a, 228b snap back into place and the pawls 230a, 230b rest above the board 234 and lock the PCBA 108 onto the motor cap 106.

Figure 14:
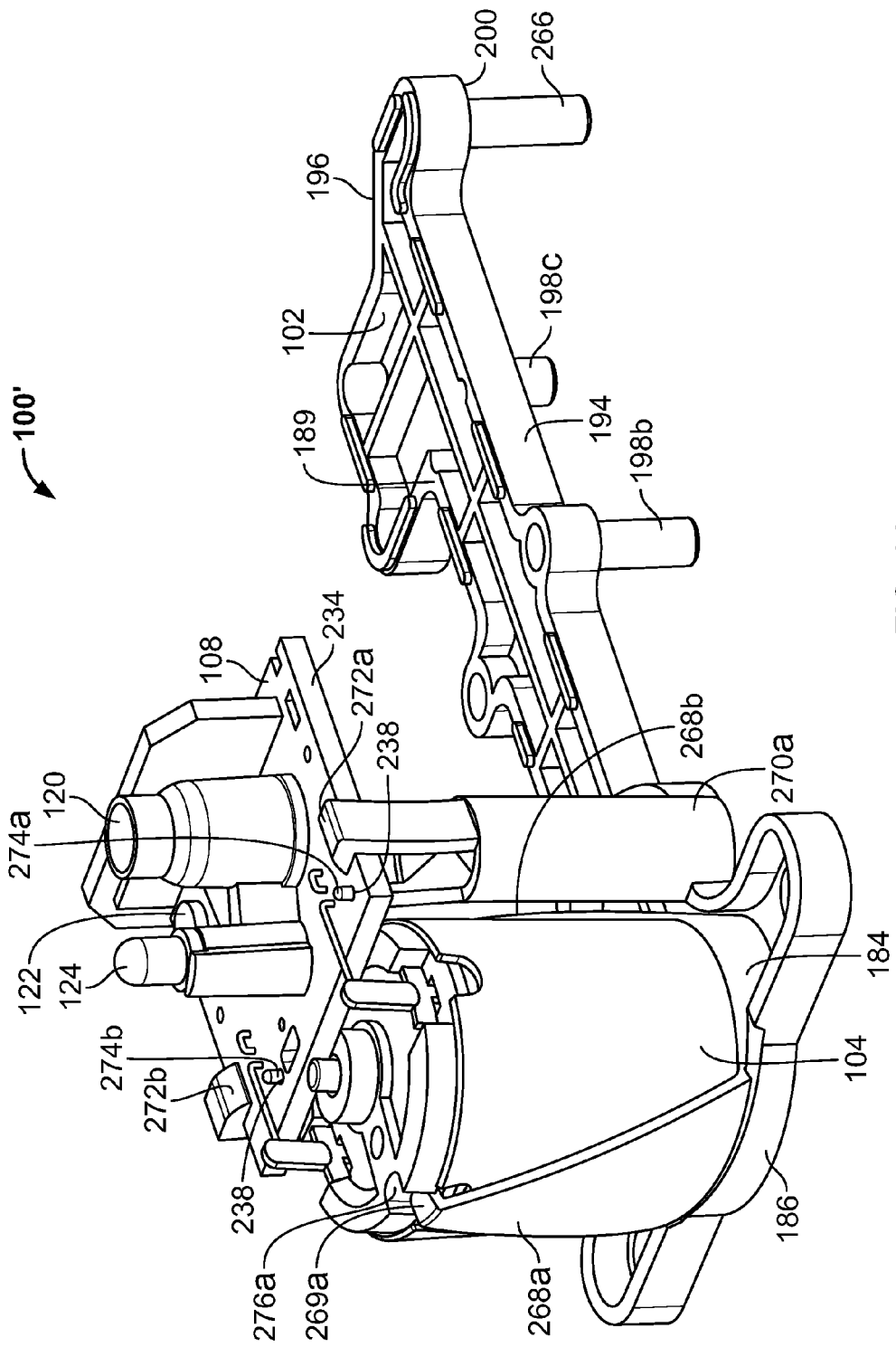
FIG. 14 is an isometric view of a second embodiment of a drive module assembly including a gear plate, a motor, and a printed circuit board, wherein a gear train is omitted for purposes of clarity.
Figure 15:
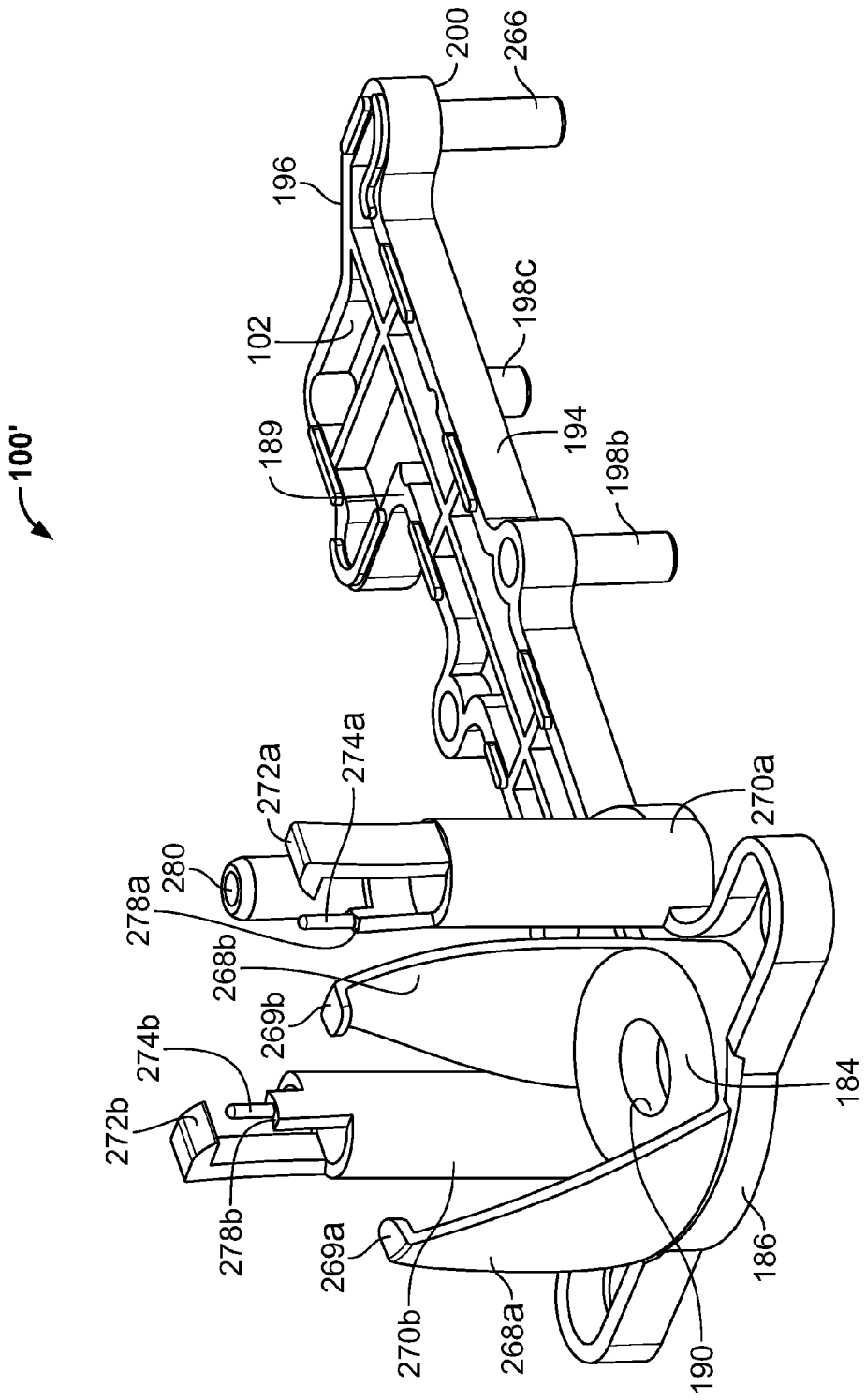
FIG. 15 is an isometric view of the drive module assembly of FIG. 14, wherein the motor and printed circuit board are omitted for purposes of clarity.

Turning to FIGS. 14 and 15, another embodiment of a drive module assembly 100' is depicted, which is identical to the previously described embodiment except for the below noted differences. One particular difference is that in this embodiment the drive module assembly 100' may be assembled without the motor cap 106. As shown in FIGS. 14 and 15, the seat 184 of the gear plate 102 includes two curved support members 268a, 268b extending from the upper surface 189 of the gear plate 102. The support members 268a, 268b of the present embodiment are disposed generally opposite one another about the seat 184. Further, the support members 268a, 268b are substantially triangular in shape and each taper inwardly to an upper end thereof, which include pawls 269a, 269b. Still further, while the present support members 268a, 268b are generally uninterrupted, other embodiments could include apertures or cutaway portions therein.

Two PCBA supports 270a, 270b also extend upwardly from the upper surface 189 of the gear plate 102. The PCBA supports 270a, 270b of the present embodiment are substantially cylindrical in shape. However, in other embodiments, different geometric shapes are utilized, e.g., rectangular or triangular. The PCBA supports 270a, 270b include pawls 272a, 272b, and guide posts 274a, 274b extending from upper surfaces of the PCBA supports 270a, 270b, respectfully.

To assemble the drive module assembly 100', the motor 104 is pressed within the curved support members 268a, 268b, thereby causing the curved support members 268a, 268b to flex outwardly and for the motor 104 to be seated therein. The motor 104 of the present embodiment includes grooves 276a, 276b (only 276a is shown), which are aligned with the pawls 269a, 269b, on the upper ends of the support members 268a, 268b. The grooves 276a, 276b may comprise any shape and may be provided in numbers greater than two about the base of the motor 104 to allow for ease of assembly. In an assembled position the motor 104 is disposed between the curved support members 268a, 268b on the seat 184 of the gear plate 102 and the pawls 269a, 269b snap into the corresponding grooves 276a, 276b of the motor 104 to hold it in place. The drive shaft 204 of the motor 104 extends through the gear plate 102 in a similar manner as discussed above. It is anticipated that the pins 192 on the gear plate 102 and the holes 208 on the motor 104 as previously described may be omitted (but it is not necessary to do so) as the pawls 269a, 269b and curved support members 268a, 268b are adapted to prevent torsional motion of the motor 104.

After the motor 104 is disposed within the seat 184, the PCBA 108 is then attached to the assembly 100'. The holes 238 in the board 234 align with and receive the guide posts 274a, 274b of the PCBA supports 270a, 270b, respectively. When the board 234 is in position, a bottom side thereof rests on two axial restraining surfaces 278a, 278b disposed adjacent guide posts 274a, 274b, respectfully, to support the board 234. Further, the pawls 272a, 272b snap over the board 234 to lock the PCBA 108 in place. A post 280 is also provided that extends from the upper surface 189 of the gear plate 102 to contact the bottom side of the board 234 to provide additional support to the PCBA 108.

Figure 16:
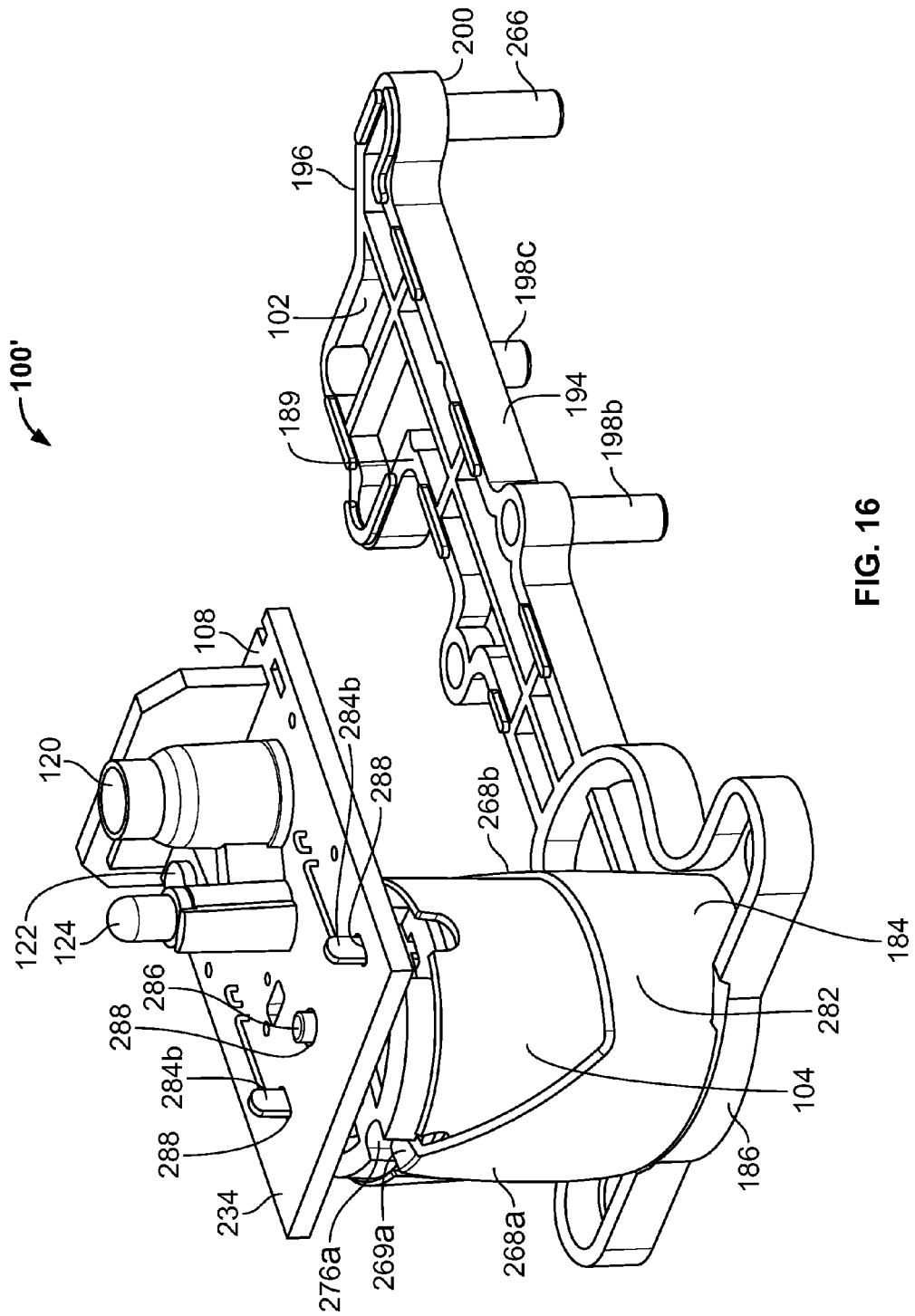
FIG. 16 is an isometric view of a third embodiment of a drive module assembly including a gear plate, a motor, and a printed circuit board, wherein a gear train is similarly omitted for purposes of clarity.

Other modifications can be made to the drive module assembly 100' without departing from the spirit of the present disclosure. For example, as shown in FIG. 16, the PCBA 108 may be attached directly to the motor 104 using welding, adhesives, or other techniques known in the art, prior to attaching the motor 104 to the assembly 100'. The motor 104 and PCBA 108 may then be attached to the assembly 100' as a single unit without the need for PCBA supports (see FIG. 16). As described above, motor support members 268a, 268b snap over the motor 104 to hold the motor 104 and PCBA 108 within the drive module assembly 100'. Further, the seat 184 may include a shroud 282, which fully or partially surrounds the motor 104 to provide additional support when the motor is attached to the assembly 100'. Still further, as shown in FIG. 16, the motor 104 may include motor terminals 284a, 284b and a post 286, which extend from an upper surface thereof and through holes 288 provided in the PCBA 108 to help align and/or retain the PCBA 108 on the motor 104.

Referring now to FIG. 2, a first pinion gear 242 is disposed on the drive shaft 204 of the motor 104, which extends through the integral gear plate 102. The first pinion gear 242 meshes with a first large gear 244, wherein the first large gear 244 includes a second pinion gear 246. The first large gear 244 and second pinion gear 246 are disposed on the axle 198a and are both rotatable about same. The second pinion gear 246 meshes with a second large gear 248, wherein the second large gear 248 include a third pinion gear 250 (shown in FIG. 13) and both the second large gear 248 and the third pinion gear 250 are disposed on and rotatable around the axle 198b. The third pinion gear 250 meshes with a sector gear 252 that is disposed on and rotatable around the axle 198c.

After assembly, the gear plate 102, the motor 104, the motor cap 106, the PCBA 108, and the gear train 109, i.e., the drive module assembly 100, can be singularly inserted into the dispenser 110 (see FIGS. 10 and 11). The drive module assembly 100 is disposed between the inner rear panel 146 and the outer rear panel 148 of the housing 126. Distal ends of the axles 198a, 198b, 198c extend into holes 254a, 254b, 254c (shown in FIG. 12), respectively, provided on an inner surface 256 of the outer rear panel 148. The drive module assembly 100 may be attached to the dispenser 110 by screws or other attachment means known in the art. Being able to singularly insert the assembled drive module assembly 100 into the device makes the device easier to manufacture and more labor efficient to assemble than if the drive module components were inserted piece-by-piece into the dispenser. The drive module assembly 100 may also be manufactured as a single unit and then singularly inserted into a variety of different dispensers. This is beneficial because it allows a manufacturer to offer a consumer a variety of different dispensers without having to redesign the entire drive module. Additionally, the snap-in engagement features of the individual components creates a more labor efficient assembly of the drive module than drive modules with components that must be screwed together. Further, having the axles 198a-c extend from a singular gear plate 102 allows for better alignment of the gears. The ability to have greater control over alignment of the gears allows for closer tolerances between the gears comprising the gear train 109, thereby providing the benefit of reduced noise during operation of the dispenser.

Still referring to FIGS. 10 and 11, the actuation of this embodiment of the drive module assembly 100 of the dispenser 110 will be described. Activation of the dispenser 110 may be initiated by manual input, i.e., a user pressing the pushbutton 162, sensory input, and/or the lapsing of a time interval. When the dispenser 110 is activated, the drive shaft 204 of the motor 104 is driven in a clockwise direction. Clockwise rotation of the draft shaft 204 causes the first pinion gear 242 to similarly rotate in a clockwise direction. The first pinion gear 242 meshes with and drives the first large gear 244 and the second pinion gear 246 in a counter-clockwise direction. The second pinion gear 246 drives the second large gear 248 and the attached third pinion gear 250 (shown in FIG. 13) in a clockwise direction. The third pinion gear 250 meshes with the sector gear 252 causing the sector gear 252 to rotate in a counter-clockwise direction.

With reference to FIGS. 10 and 11, a rod 258 extends from an upper end 260 of the sector gear 252. The rod 258 is provided within the circular aperture 178 of the attachment portion 176 of the actuator arm 126. As the sector gear 252 rotates in a counter-clockwise direction, the rod 258 is rotated in a downward direction. As the rod 258 rotates it impinges on portions of the actuator arm 126 defining the circular aperture 178, thereby similarly pulling the actuator arm 126 downwardly. Downward movement of the actuator arm 126 causes the overhang portion 174 thereof to depress the valve stem 114 of the aerosol container 112, which causes the subsequent release of fluid from the container 112. The fluid is thereafter emitted through a dispensing bore 262 provided within the overhang portion 174 of the actuator arm 126 and into the atmosphere. The downward path of the actuator arm 126 has a direction that is parallel to a longitudinal axis 264 of the container 112. Two posts 266, which project from the gear plate 102, interfere with the sector gear 252 to prevent the sector gear 252 from pulling the actuator arm 126 too far down on the valve stem 114. The length of time the actuator arm 126 is held in the discharge position is the spraying period. The duration of the spraying period could range anywhere from a fraction of a second to one or more seconds depending on the amount of fluid that is desired to be released from the container 112. Indeed, if desired, the actuator arm 126 could be held in the discharge position until all of the container contents are exhausted. It is also contemplated that the container 112 could have a metered valve stem, which releases a specific amount of fluid independent of the duration of time the actuator arm 126 is held in the discharge position.

Upon completion of a spraying sequence, the motor 104 is energized in a second direction to reverse the direction of rotation of the drive shaft 204. The rotation of the drive shaft 204 in the counter-clockwise direction causes the above-noted gears to similarly rotate in an opposite direction causing the rod 258 of the sector gear 252 to rotate in an upward direction. The upward motion of the rod 258 forces the actuator arm 126 upwardly, thereby allowing the valve stem 114 of the container 112 to return to a pre-actuated position due to the upward force provided by the valve assembly, at which time the valve assembly is closed and terminates further spraying.

Figure 19:
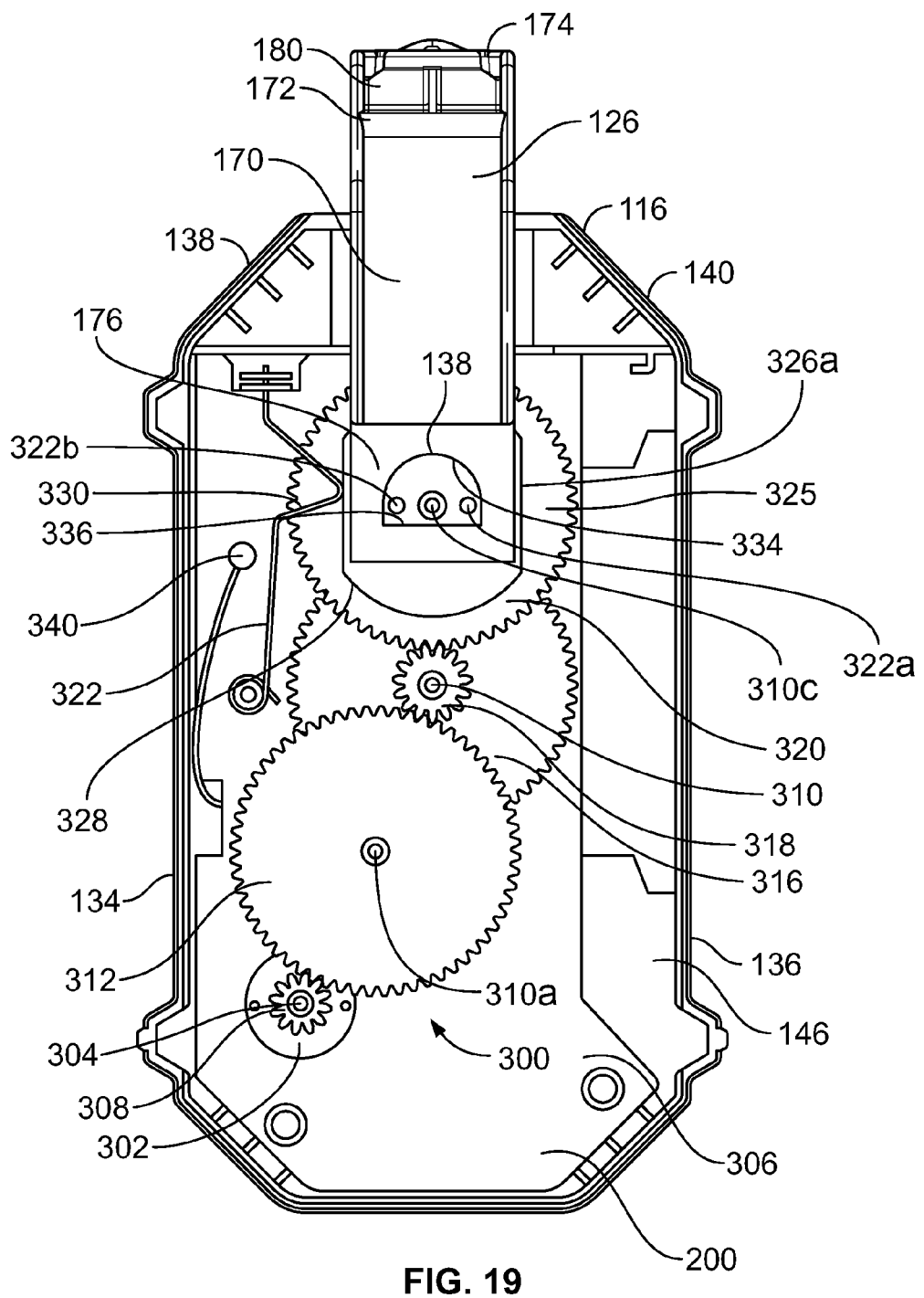
FIG. 19 is a view similar to FIG. 17, except that an actuator arm has been included.

FIGS. 17-19 show an alternative embodiment of a drive module assembly 300 designed to use a unidirectional motor 302. A drive shaft 304 of the unidirectional motor 302 extends through a modified integral gear plate 306 and has a first pinion gear 308 thereon. A first axle 310a on the integral gear plate 306 receives a first large gear 312 and a second pinion gear (not shown). A second axle 310b receives a second large gear 316 and a third pinion gear 318 and a third axle 310c receives a cam gear 320. The cam gear 320 includes a rimmed portion 324 disposed on an upper surface 325 thereof. A first and a second pin 322a, 322b, respectively, are disposed on the rimmed portion 324 on opposing sides of the third axle 310c. The rimmed portion 324 also includes two detents 326a, 326b on an outer surface 328 thereof. A bent section 330 of a spring 332, which is disposed on the integral gear plate 306, rides along the outer surface 328 of the rimmed portion 324 of the cam gear 320. The actuator arm 126 in the present embodiment includes a u-shaped cutout cam section 334 disposed in the attachment portion 176 thereof. The u-shaped cutout cam section 334 includes a flat side 336 and a rounded section 338. The u-shaped cutout cam section 334 is designed to receive the two pins 322a, 322b when the actuator arm 126 is inserted into the housing 116.

When the motor 302 is initially activated either by the manual pushbutton 162, the sensor 120, and/or the lapsing of a time interval, the drive shaft 304 and the first pinion gear 308 are rotated in a clockwise direction. The first pinion gear 308 meshes with the first large gear 312 causing the first large gear 312 and the attached second pinion gear (not shown) to rotate in a counter-clockwise direction. The second pinion gear meshes with the second large gear 316 and the attached third pinion gear 318 to cause the second large gear 316 and the third pinion gear 318 to rotate in a clockwise direction. The third pinion gear meshes with the cam gear 320, thereby causing the cam gear 320 to rotate in a counter-clockwise direction. As the cam gear 320 rotates, the pins 322a, 322b revolve around the axle 310c in a counter-clockwise direction. As the pins 322a, 322b move, the first pin 322a contacts the flat side 336 of the cutout cam section 334 of the actuator arm 126. The pin 322a pushes down on the flat side 336 of the cutout cam section 334, thereby causing the actuator arm 126 to move downwardly and depress the valve stem 114 of the container 112 in the same manner as described above. As the first pin 322a is pushing on the flat side 336 the second pin 322b is able to revolve within the rounded section 338 of the cutout cam section 334. As the pins 322a, 322b continue to revolve, the first pin 322a passes the flat side 336 of the cutout cam section 334. When the downward force is removed from the actuator arm 126, the actuator arm 126 and the valve stem 114 then move upwardly to the pre-actuation position in response to the upward force provided by the valve assembly, at which time the valve assembly of the container 112 is closed.

The initial activation of the motor 302 by either the manual pushbutton 162, the sensor 120, and/or the lapsing of a time interval, rotates the cam gear 300 to cause the bent section 330 of the spring 332 to move out of the detent 326b and ride along the outer surface 328 of the rimmed portion 324, thereby causing the spring 332 to contact and activate a spring switch 340 disposed on the gear plate 306 (see FIG. 18). The motor 302 continues to run until the bent section 330 of the spring 332 rides into the second detent 326a, thereby causing the spring 332 to move off of the spring switch 340. When the spring switch 340 is opened the motor 302 is turned off. The pins 322a, 322b are positioned on the cam gear 320 such that when the spring 332 enters one of the detents 326a, 326b to turn the motor 302 off, the actuator arm 126 is in the pre-actuation position. Although the preferred embodiment describes the cutout cam section 334 as u-shaped, it is contemplated that the cutout cam section 334 could be any shape that would allow the pins to contact a side of the cutout to pull the actuator arm in a downward direction.

Figure 20:
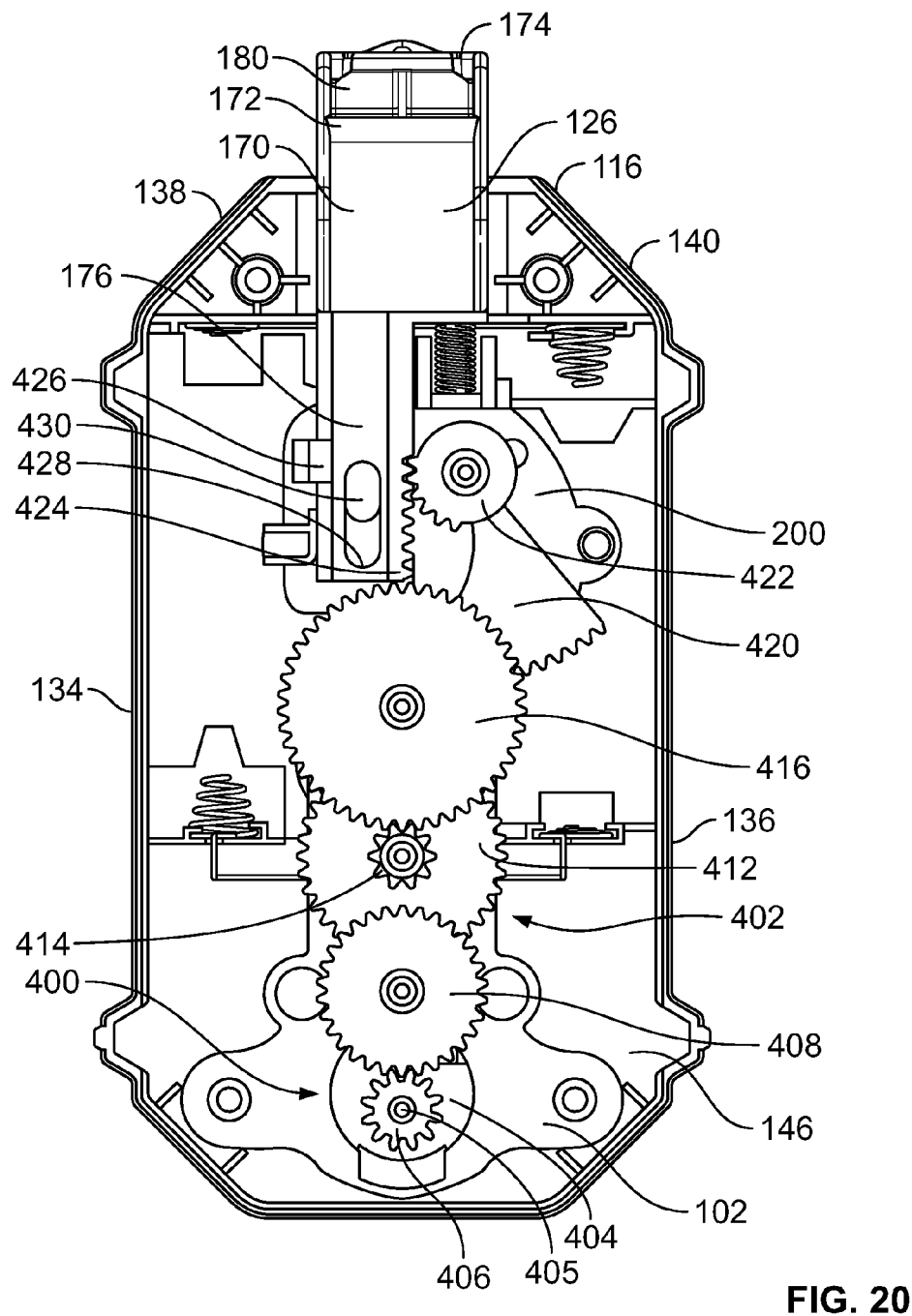
FIG. 20 is a rear elevational view of a fifth embodiment for a drive module assembly disposed in a dispenser.

In a further embodiment, illustrated in FIG. 20, a drive module assembly 400 is adapted to have a gear train 402 with a higher gear ratio, which allows the drive module assembly 400 to use a smaller and more efficient motor 404. The gear train 402 includes a first pinion gear 406 attached to a drive shaft 405 of the motor 404, a first large gear 408 and attached second pinion gear (not shown), a second large gear 412 and attached third pinion gear 414, a third large gear 416 and attached fourth pinion gear (not shown), and a sector gear 420 and attached fifth pinion gear 422. The fifth pinion gear 422 meshes with a rack 424 disposed on the attachment portion 176 of the actuator arm 126. The gear plate 102 is adapted to include a capture pawl 426 extending from the underside 200 of the gear plate 102. The actuator arm 126 is constrained on the gear plate 102 by the capture pawl 426, which allows the actuator arm 126 to become part of the module drive assembly 400, thereby providing easy module assembly. A racetrack-shaped slot 428 is provided in the attachment portion 176 of the actuator arm 126. The racetrack-shaped slot 428 receives a racetrack-shaped rod 430 disposed on the underside 200 of the gear plate 102. The rod 430 constrains the movement of the actuator arm 126 in the longitudinal direction. Additionally, a spring 432 is provided below the actuator arm 126 to assist the valve assembly of the container 112 in overcoming the higher tare torque of the gear train 402 to raise the actuator arm 126 to a pre-actuation position when the motor 404 is deactivated.

During activation, the motor 404 drives the first pinion gear 406 in a counter-clockwise direction causing the first large gear 408 and the attached second pinion gear to rotate in a clockwise direction. The second pinion gear causes the second large gear 412 and the attached third pinion gear 414 to rotate in a counter-clockwise direction. The third pinion gear 414 rotates the third large gear 416 and the attached fourth pinion gear in a clockwise direction, which causes the sector gear 420 and the attached fifth pinion gear 422 to rotate in a counter-clockwise direction. The rotation of the fifth pinion gear 422 in the counter-clockwise direction causes the rack 424 on the attachment portion 176, and ultimately the actuator arm 126, to be pulled downwardly, thereby releasing fluid from the aerosol container 112 as described above.

Figure 21:
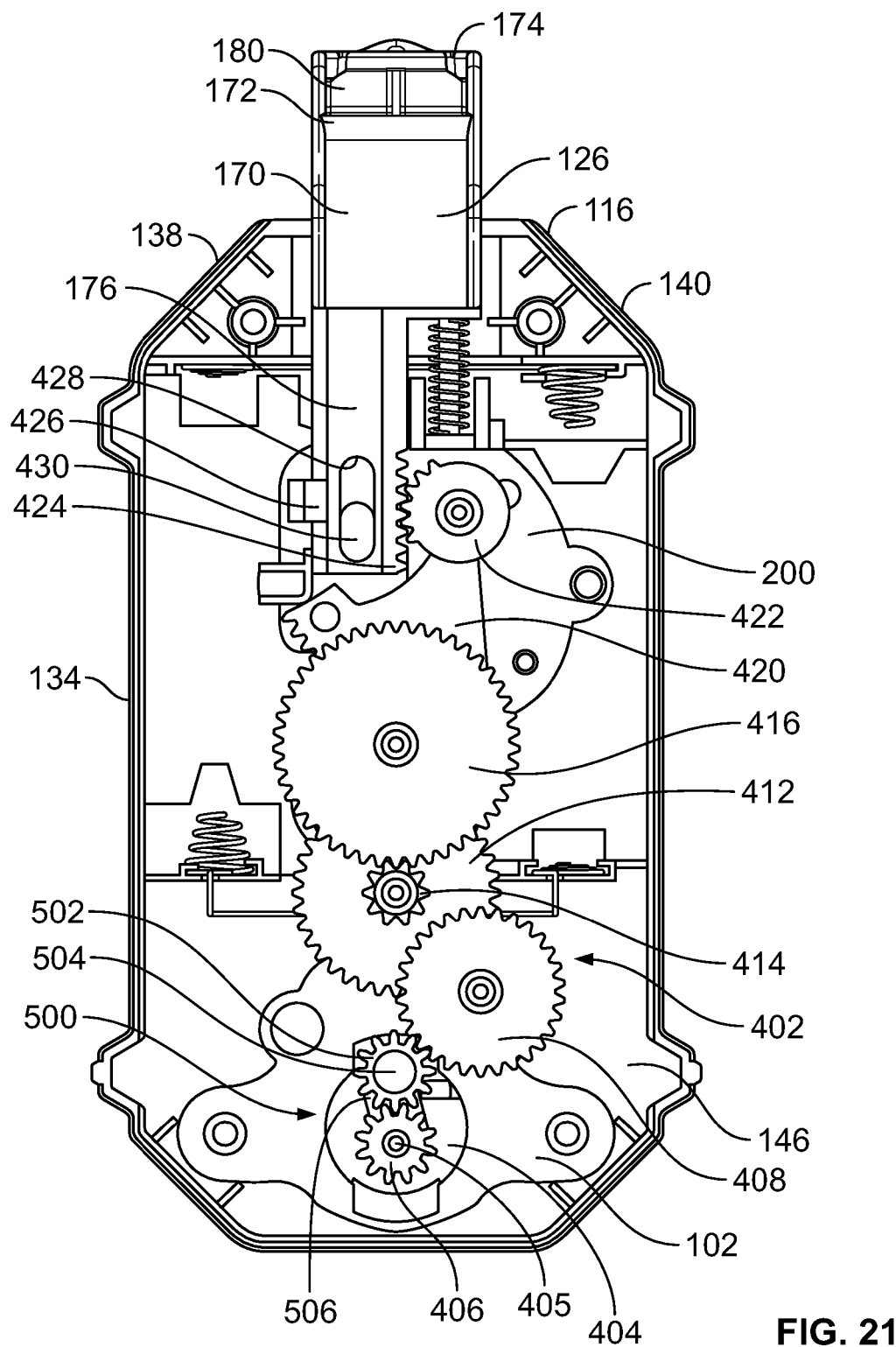
FIG. 21 is a rear elevation view of a sixth embodiment for a drive module assembly disposed in a dispenser.
Figure 22:
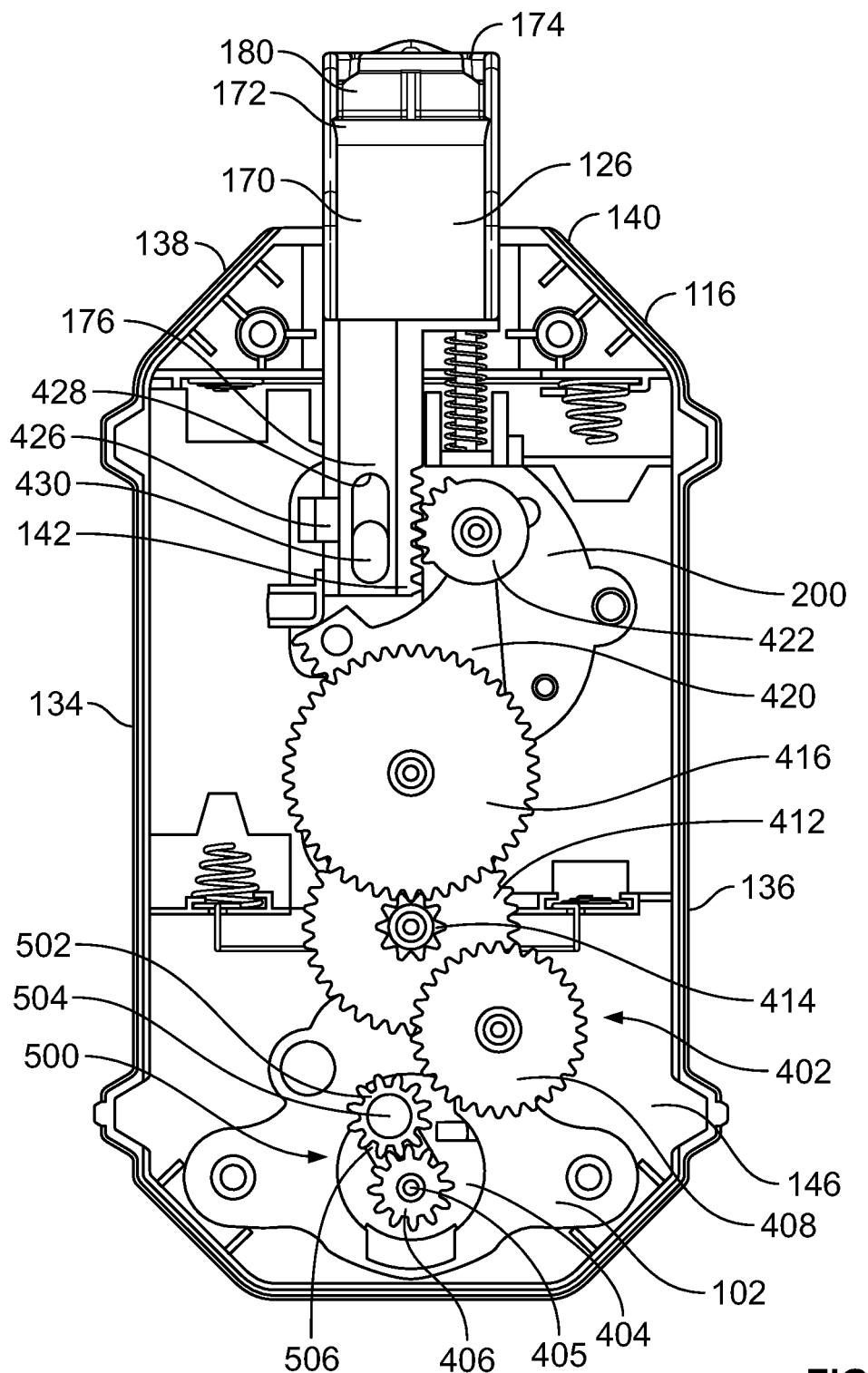
FIG. 22 is a view similar to FIG. 21, except the drive module assembly is in a disengaged position.

Referring now to FIGS. 21 and 22, another embodiment of a drive module assembly 500 is illustrated, which is also adapted to have a gear train 402 with a higher gear ratio to allow the assembly 500 to use a smaller and more efficient motor 404. This embodiment 500 is similar to and operates in substantially the same way as the third embodiment 400 except for the below noted differences, wherein like components are given like reference numerals. One particular difference is the provision of an idler gear 502 between the first pinion gear 406 and the first large gear 408 of the gear train 402. The idler gear 502 is attached to an axle 504 connected to one end of a swing arm 506. A second end of the swing arm 506 is attached to the drive shaft 405. The swing arm 506 allows the idler gear 502 to pivot around the drive shaft 405 and the first pinion gear 406. Upon activation of the motor 404, the drive shaft 405 and the first pinion gear 406 are rotated in a clockwise direction causing the swing arm 506 to also rotate in a clockwise direction. The clockwise rotation of the swing arm 506 pivots the idler gear 502 into engagement with the first large gear 408 to cause the first large gear 408 to rotate in the clockwise direction (shown in FIG. 21). The gear train 402 transmits the rotation in a similar manner as noted above to cause the actuator arm 126 to be pulled downwardly, thereby depressing the valve stem 114 and causing fluid to be released from the container 112. Upon completion of the spraying sequence, the motor 404 is reenergized in the counter-clockwise direction thereby causing the swing arm 506 to throw the idler gear 502 out of engagement with the first large gear 408 (see FIG. 22). When the idler gear 502 is in a disengaged position with the first large gear 408 the internal motor tare torque and generator drag is removed from the gear train 402, thereby allowing the actuator arm 126 to return to a pre-actuation position due to the spring 432 and the internal upward forces of the valve assembly.

With regard to the embodiments depicted in FIGS. 1-22, the drive module assemblies may have numerous varying characteristics. For example, as noted previously, the actuator arm 126 is driven in a direction parallel to the longitudinal axis 264 of the container 112, however, the drive module assemblies may be modified to cause the overhang portion 174 of the actuator arm 126 to impart a force onto any area of the valve stem 114 to depress or tilt same.

It is also envisioned that different alternatives of the drive assemblies may be modified to be used in dispensers that have the ability to hold and spray one or more containers having the same or different products. Further, the drive module assemblies could spray the contents of the containers at the same time or at selected intervals and sequences.

It should be apparent to one skilled in the art that any of the disclosed module drive assemblies may be used with a dispenser having any of the structural and functional characteristics of the engagement mechanisms described in U.S. patent application Ser. No. 11/725,402. Further, it is anticipated that module dispensing mechanisms may be adapted to be used with any dispenser known in the art used to release the contents of an aerosol container.

INDUSTRIAL APPLICABILITY

The assembly described herein advantageously allows for all the components of a drive module to be mounted together, without screws, and then singularly placed into a housing of a dispenser. The snap-together features of the components and the ability to singularly place the drive module assembly into a dispenser makes the dispenser easier and more labor efficient to manufacture.

Numerous modifications will be apparent to those skilled in the art in view of the foregoing description. Accordingly, this description is to be construed as illustrative only and is presented for the purpose of enabling those skilled in the art to make and use what is herein disclosed and to teach the best mode of carrying out same. The exclusive rights to all modifications which come within the scope of this disclosure are reserved.

We claim:

1. A drive module assembly, comprising:
    a drive motor including a drive shaft;
    a gear plate including a seat for retaining the drive motor within the seat, wherein at least one support member extends from an upper surface of the gear plate toward the drive motor;
    a motor cap to engage a surface of the drive motor opposite the drive shaft and having at least one pawl for snap-fitting into the support member of the seat; and
    at least one axle, which is adapted to receive a gear.

2. The assembly of claim 1, wherein the motor cap includes two pawls.

3. The assembly of claim 1 further including a printed circuit board assembly.

4. The assembly of claim 3, wherein the motor cap includes at least one engagement portion adapted to retain the printed circuit board assembly.

5. The assembly of claim 4, wherein the engagement portion includes at least one additional pawl.

6. The assembly of claim 4, wherein the engagement portion includes at least one post.

7. The assembly of claim 1, wherein the gear plate further includes a plurality of axles.

8. The assembly of claim 1, wherein the at least one support member of the seat includes opposing curved support members adapted to retain the at least one pawl of the motor cap.

9. The assembly of claim 8 further including pins disposed on the seat to receive the motor.

10. The assembly of claim 9 further including holes disposed on a side of the motor to mate with the pins on the seat.

11. The assembly of claim 7, wherein the assembly is manufactured as a single unit and can be singularly inserted into a dispenser.

12. A method for assembling a drive module, comprising the steps of:
    providing a gear plate with a seat for a motor having a drive shaft, at least one axle, and at least one support member extending from an upper surface of the gear plate;
    retaining the motor within the seat, wherein the at least one support member extends toward the motor;
    providing a motor cap with at least one pawl, wherein the at least one pawl snaps into the support member of the seat and the motor cap covers a surface of the motor opposite the drive shaft; and
    disposing a gear train on the at least one axle.

13. The method of claim 12, wherein the step of retaining the motor within the seat further includes the step of snapping a motor cap into the gear plate over the surface of the motor opposite the drive shaft.

14. The method of claim 13, wherein the step of retaining the motor within the seat further includes the step of mating holes disposed on a side of the motor with pins disposed on the seat.

15. The method of claim 12, further including the step of providing a printed circuit board assembly.

16. The method of claim 15, further including the step of providing at least one engagement portion adapted to retain the printed circuit board.

17. A dispensing system, comprising:
    a housing;
    a container having a product therein; and
    a drive module assembly adapted to release the product from a dispensing system, the drive module assembly comprising:
        a drive motor including a drive shaft;
        a gear plate including a seat for retaining the drive motor, wherein at least one support member extends from an upper surface of the gear plate toward the drive motor;
        a motor cap to engage a surface of the drive motor opposite the drive shaft, the motor cap having two pawls disposed on a bottom side for snap-fitting into the at least one support member of the seat, and two pawls extending from an upper side of the motor cap;
        at least one axle, which is adapted to receive a gear.

18. The assembly of claim 17, further including at least one gear.

19. The assembly of claim 17, wherein the at least one support member of the seat includes opposing curved support members adapted to retain the two pawls of the motor cap.

20. The assembly of claim 17 further including holes disposed on a side of the motor to mate with pins disposed on the seat.

* * * * *